United States Patent
Mohan et al.

(10) Patent No.: US 9,784,670 B1
(45) Date of Patent: Oct. 10, 2017

(54) UNIFIED DETECTION SYSTEM FOR FLUOROMETRY, LUMINOMETRY AND SPECTROMETRY

(71) Applicant: Theranos, Inc., Palo Alto, CA (US)

(72) Inventors: Karan Mohan, Palo Alto, CA (US); Samartha Anekal, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 138 days.

(21) Appl. No.: 14/602,189

(22) Filed: Jan. 21, 2015

Related U.S. Application Data

(60) Provisional application No. 61/930,357, filed on Jan. 22, 2014.

(51) Int. Cl.
  *G02B 26/08* (2006.01)
  *G01N 21/00* (2006.01)
  (Continued)

(52) U.S. Cl.
  CPC ....... *G01N 21/255* (2013.01); *G01N 21/6486* (2013.01); *G01N 21/76* (2013.01);
  (Continued)

(58) Field of Classification Search
  CPC .. G01N 21/255; G01N 21/76; G01N 21/6486; G01N 2201/061;
  (Continued)

(56) References Cited

U.S. PATENT DOCUMENTS

| 3,854,044 A | 12/1974 | Stay et al. |
| 5,070,332 A | 12/1991 | Kaller et al. |
(Continued)

FOREIGN PATENT DOCUMENTS

| CN | 1431475 A | 7/2003 |
| CN | 201156031 | 11/2008 |
(Continued)

OTHER PUBLICATIONS

Advisory Action dated Feb. 8, 2016 for U.S. Appl. No. 13/951,449.
(Continued)

*Primary Examiner* — James Phan

(57) ABSTRACT

The devices and systems disclosed herein provide multiple optical capabilities in a single device or system. Methods for using these devices and systems are provided. These devices and systems are configurable for operation in each of a spectroscopy mode, a fluorescence mode, and a luminescence mode, and are capable of performing spectroscopic, fluorescence, and luminescence observations, measurements, and analyses when operated in the corresponding spectroscopy mode, fluorescence mode, or luminescence mode. These devices and systems include mirror dispersion elements having multiple faces including an optical dispersion element on one face (e.g., a diffraction grating or a prism) and a reflective element on another face (e.g., a mirror). These multiple capabilities eliminate the need to move or load a sample in multiple devices when subjecting a sample to multiple analyses, and thus provide greater accuracy, precision, and speed while reducing complexity and cost of sample analysis.

8 Claims, 9 Drawing Sheets

(51) Int. Cl.
  *G01N 21/25* (2006.01)
  *G01N 21/76* (2006.01)
  *G01N 21/64* (2006.01)
  *G02B 5/08* (2006.01)
  *G02B 27/42* (2006.01)
  *G02B 5/18* (2006.01)
  *G02B 5/04* (2006.01)
  *G02B 7/182* (2006.01)

(52) U.S. Cl.
  CPC .............. *G02B 5/04* (2013.01); *G02B 5/08* (2013.01); *G02B 5/18* (2013.01); *G02B 7/182* (2013.01); *G02B 27/42* (2013.01); *G01N 2201/061* (2013.01); *G01N 2201/068* (2013.01)

(58) Field of Classification Search
  CPC ....... G01N 2201/068; G01N 2021/135; G02B 5/08; G02B 5/18; G02B 5/04; G02B 7/182; G02B 27/42; G02B 2/10; G02B 2/105; G02B 2/106; G02B 2/108
  USPC ............... 359/588, 563, 566, 211.1–212.2, 359/201.1–202.1, 207.7, 838, 872; 356/246, 440, 72; 422/63, 52
  See application file for complete search history.

(56) References Cited

U.S. PATENT DOCUMENTS

| | | |
|---|---|---|
| 5,414,508 A | 5/1995 | Takahashi et al. |
| 6,088,097 A | 7/2000 | Uhl |
| 6,344,651 B1 | 2/2002 | Woolaway et al. |
| 6,396,580 B1 | 5/2002 | Tewes |
| 6,599,475 B1 | 7/2003 | Berndt et al. |
| 7,005,646 B1 | 2/2006 | Jordanov et al. |
| 7,250,893 B2 | 7/2007 | Todoroff et al. |
| 7,605,357 B2 | 10/2009 | Fathimulla et al. |
| 8,313,713 B2 | 11/2012 | Jacobs et al. |
| 8,948,610 B2 | 2/2015 | Azadeh et al. |
| 2001/0028497 A1 | 10/2001 | Uhl |
| 2002/0154364 A1 | 10/2002 | Green et al. |
| 2003/0104494 A1 | 6/2003 | Ravkin et al. |
| 2003/0202905 A1 | 10/2003 | Devlin et al. |
| 2003/0236458 A1 | 12/2003 | Hochman |
| 2004/0126005 A1 | 7/2004 | Duvdevani et al. |
| 2004/0239923 A1 | 12/2004 | Adams et al. |
| 2005/0116778 A1 | 6/2005 | Braier et al. |
| 2005/0153435 A1 | 7/2005 | Archibald |
| 2006/0043301 A1 | 3/2006 | Mantele et al. |
| 2006/0215400 A1 | 9/2006 | Lewis et al. |
| 2006/0261994 A1 | 11/2006 | Todoroff et al. |
| 2007/0035818 A1 | 2/2007 | Bahatt et al. |
| 2009/0190822 A1 | 7/2009 | Ortyn et al. |
| 2010/0014158 A1 | 1/2010 | Nihoshi |
| 2010/0128256 A1 | 5/2010 | Thomson |
| 2010/0172656 A1 | 7/2010 | Saitou et al. |
| 2011/0064628 A1 | 3/2011 | Thomas et al. |
| 2011/0242535 A1 | 10/2011 | Frose |
| 2011/0293293 A1 | 12/2011 | Sugimoto |
| 2011/0318015 A1 | 12/2011 | Sugimoto |
| 2012/0039615 A1 | 2/2012 | Cho et al. |
| 2013/0088221 A1 | 4/2013 | Van et al. |
| 2014/0030737 A1 | 1/2014 | Holmes et al. |
| 2014/0038206 A1 | 2/2014 | Holmes et al. |
| 2014/0193892 A1 | 7/2014 | Mohan et al. |
| 2014/0273188 A1 | 9/2014 | Mohan et al. |
| 2015/0031051 A1 | 1/2015 | Mohan et al. |
| 2016/0018328 A1* | 1/2016 | Kim ............... G01N 21/9501 356/237.5 |
| 2016/0072453 A1 | 3/2016 | Mohan et al. |

FOREIGN PATENT DOCUMENTS

| | | |
|---|---|---|
| CN | 201319584 | 9/2009 |
| CN | 102427335 A | 4/2012 |
| EP | 0781987 A2 | 7/1997 |
| JP | 2006162427 | 6/2006 |
| JP | 2007127449 A | 5/2007 |
| JP | 2010091679 | 4/2010 |
| JP | 2010091809 | 4/2010 |
| JP | 2011118264 | 6/2011 |
| TW | 201224425 A | 6/2012 |
| WO | 2002093141 A1 | 11/2002 |
| WO | 2009142312 | 11/2009 |
| WO | 2012178069 A | 12/2012 |
| WO | 2014018805 A2 | 1/2014 |
| WO | 2014127372 A2 | 8/2014 |
| WO | 2014145963 A2 | 9/2014 |

OTHER PUBLICATIONS

Advisory Action dated Apr. 28, 2016 for U..S Appl. No. 13/951,063.
Notice of Allowance dated Mar. 25, 2016 for U.S. Appl. No. 13/951,449.
Notice of Allowance dated Apr. 14, 2016 for U.S. Appl. No. 14/161,639.
Office Action dated Feb. 24, 2016 for U.S. Appl. No. 13/951,063.
Office Action dated May 12, 16 for U.S. Appl. No. 14/508,137.
Office Action dated Sep. 9, 2016 for U.S. Appl. No. 14/508,137.
Office Action dated May 6, 2015 for U.S. Appl. No. 13/951,449.
Office Action dated Jun. 12, 2015 for U.S. Appl. No. 14/161,639.
Office Action dated Jun. 5, 2015 for U.S. Appl. No. 14/508,137.
International Search Report and Written Opinion dated Sep. 11, 2014 for Application No. PCT/US2014/016962.
The International Search Report and the Written Opinion dated Mar. 24, 2014 for Application No. PCT/US2013/052141.
U.S. Appl. No. 14/600,630, filed Jan. 20, 2015.
Office Action dated Jan. 15, 2016 for U.S. Appl. No. 14/508,137.
Office Action dated Jan. 4, 2016 for U.S. Appl. No. 14/161,639.
Office Action dated Jul. 8, 2015 for U.S. Appl. No. 13/951,063.
International Search Report dated May 5, 2016 for PCT/US2014/030823.
Notice of Allowance dated Jul. 20, 2016 for U.S. Appl. No. 14/849,264.
Office Action dated Spr. 11, 2017 for U.S. Appl. No. 15/160,900.
Office Action dated May 19, 2016 for U.S. Appl. No. 14/849,264.

* cited by examiner

UNIFIED DETECTION SYSTEM FOR FLUOROMETRY, LUMINOMETRY AND SPECTROMETRY

CROSS-REFERENCE TO RELATED APPLICATION

This application claims priority to, and the benefit of, U.S. Provisional Patent Application Ser. No. 61/930,357, filed Jan. 22, 2014, which Provisional Patent Application is hereby incorporated by reference in its entirety.

BACKGROUND

Analysis of biological samples from a subject may be important for health-related diagnosing, monitoring, or treating of the subject. A variety of methods are known for the analysis of biological samples. For example, many methods for analyzing biological samples utilize optical methods and techniques, including, e.g., imaging, absorbance measurements, spectrophotometric techniques, fluorometric techniques, luminometric techniques, and other techniques and measurements.

However, in order to provide better diagnosing, monitoring, or treating of subjects, improvements in the analysis of biological samples are desired. In particular, improved optical techniques and devices, suitable for the analysis of biological samples, are needed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Applicants disclose herein multifunctional devices and systems, each device or system being capable of performing at least three types of measurements, e.g., fluorescence measurements, luminescence measurements, and absorbance measurements. Methods disclosed herein provide methods of performing at least three types of measurements, e.g., fluorescence measurements, luminescence measurements, and absorbance measurements, using multifunctional devices or systems disclosed herein. Such measurements may be made, for example, on a biological sample, or on more than one biological sample. Measurements made using multifunctional devices or systems disclosed herein, or made using methods disclosed herein, may further be made in concert with, or prior to, or following, other measurements made on the same biological sample or samples, or on a biological sample or samples derived from, obtained along with, or similar to, a biological sample or samples measured using the devices, systems, or methods disclosed herein.

Accordingly, Applicants provide devices that are configurable for operation in each of a spectroscopy mode, a fluorescence mode, and a luminescence mode. Devices disclosed herein are capable of performing spectroscopy, fluorescence, and luminescence measurements and observations on a sample. In embodiments, spectroscopy measurements and observations performed on a sample may comprise absorbance measurements performed on a sample. Devices disclosed herein may be configured for operation in a particular mode at different times. The configurations of devices disclosed herein may be changed, so that a device may be configured for operation in a spectroscopy mode at one time, and may be configured for operation in a fluorescence mode at another time, and may be configured for operation in a luminescence mode at yet another time. Devices disclosed herein are thus configurable for performing spectroscopic measurements or observations when operated in a spectroscopy mode, for performing fluorescence measurements or observations when operating in a fluorescence mode, and for performing luminescence measurements or observations when operating in a luminescence mode.

Applicants further provide systems comprising such devices. Such systems may be configured for operation in a spectroscopy mode, a fluorescence mode, and a luminescence mode. The configurations of systems disclosed herein may be changed, so that a system may be configured for operation in a spectroscopy mode at one time, and may be configured for operation in a fluorescence mode at another time, and may be configured for operation in a luminescence mode at yet another time.

Applicants further provide methods for performing spectroscopic, fluorescence, and luminescence measurements and observations. For example, Applicants provide methods for performing spectroscopic, fluorescence, and luminescence measurements and observations on a sample, or on portions of a sample. These methods comprise the use of devices configured for operation in a spectroscopy mode, a fluorescence mode, and a luminescence mode as disclosed herein, and comprise the use of systems comprising such devices which may be configured for operation in a spectroscopy mode, a fluorescence mode, and a luminescence mode.

Thus, spectroscopic methods disclosed herein comprise the use of devices or systems configured for operation in a spectroscopy mode. In embodiments, spectroscopic methods disclosed herein may be used to make absorbance measurements. Florescence methods disclosed herein comprise the use of devices or systems configured for operation in a fluorescence mode. Luminescence methods disclosed herein comprise the use of devices or systems configured for operation in a luminescence mode.

In one embodiment, Applicants disclose a device comprising: a first optical element comprising a grating or other diffractive surface (e.g., an excitation path grating) mounted on a movable mount (which may be, e.g., a rotatable mount, a translatable mount, or other movable mount); a first mirror configured for reflecting light from said grating; a first lens (or first set of lenses) configured for focusing or for collimating light reflected from said first mirror; a second mirror mounted on a movable mount (which may be, e.g., a rotatable mount, a translatable mount, or other movable mount) and configured for reflecting light from said first lens or said first set of lenses; a second optical element mounted on a movable mount (which may be, e.g., a rotatable mount, a translatable mount, or other movable mount), having a first face and a second face, said first face having a reflective surface configured to reflect of light (e.g., light from said second mirror), and having a diffractive surface (e.g., an emission path grating) on said second face; a second lens (or second set of lenses) configured for directing light to or onto said second optical element; and a photodetector. In embodiments, such devices may comprise a sample holder configured to hold a sample for observation, measurement, or analysis, e.g., for optical observation, measurement, or analysis. In embodiments, such devices may comprise a sample handling device configured to transport a sample, a sample holder, or both, to a location suitable for observation, measurement, or analysis, e.g., for optical observation, measurement, or analysis. In embodiments, a sample handling device may comprise a fluid handling device or system, or may be configured to operate in conjunction with a fluid handling device or system. In embodiments, a sample handling device may comprise a gantry, or may be configured to operate in conjunction with a gantry. In embodiments, a fluid handling device may comprise, or be configured to operate in conjunction with, a gantry.

In embodiments, a device as disclosed herein may include a light source, and may include optical elements (e.g., one or more of a lens, a grating, an aperture, a filter, a polarizer, or other element or elements) configured to provide light for illuminating a sample. In embodiments, light source for illuminating a sample may be emitted from a light source and then pass directly to the sample. In embodiments, a light source configured for illuminating a sample may be emitted from a light source and may then pass to, onto, through, or by, a grating, a mirror, a lens, a filter, a pin-hole, or other optical element or device, prior to passing to the sample. In embodiments, light for illuminating a sample may be emitted from a light source and may be split into two or more light paths; said two or more light paths may be directed along the same, or along similar, or along different, paths. In embodiments, one or more of said two or more light paths may be directed to a sample.

In embodiments, a device as disclosed herein may comprise a mirror or other reflective surface. It will be understood that a mirror may be configured to reflect some, or may be configured to reflect substantially all, of the light impinging on that mirror from a light source, or a mirror, or a lens, or a grating, or other source.

In embodiments, a device as disclosed herein may comprise a dispersion element, e.g., a diffraction grating, diffractive lens, diffuser, beam splitter, corrective lens, or other surface or element configured to diffract light. In embodiments, a device as disclosed herein may comprise a pin-hole, or slit, or plurality of pin-holes, a slit or slits, or other optical elements configured to provide diffraction or interference with light. Diffraction (and interference) may affect transmitted, or reflected light (and, where reflected light interacts with incident light, may affect incident light as well). It will be understood that an optical element comprising a dispersion element or diffractive surface may be configured to diffract some, or substantially all, of the light impinging on, passing through, or reflected from that optical element from a light source, or a, or a lens, or a grating, or other source. It will be understood that a light source may be configured may direct some, or substantially all, of its emitted light onto a sample, or onto a surface, or onto or through a lens, or a grating, or a slit, or a hole, or other object, optical element, or location.

In embodiments, the device may be an optical measurement device. In embodiments, the device may be an optical imaging device. In embodiments, the device may be configured to measure or detect optical intensity. In embodiments, the device may be configured to measure or detect absorbance of light. In embodiments, the device may be configured to detect or measure spectral information from light passing through, or reflected from, or diffracted by, or emitted from, a sample or portion thereof. In embodiments, the device may be configured to detect or measure light scattering information from light passing through, or reflected from, or diffracted by, or emitted from, a sample or portion thereof. In embodiments, the device may be configured to detect or measure polarization information from light passing through, or reflected from, or diffracted by, or emitted from, a sample or portion thereof. In embodiments, the device may be configured to detect or measure other optical information from light passing through, or reflected from, or diffracted by, or emitted from, a sample or portion thereof.

In embodiments, a device disclosed herein may be configured for operation in a spectroscopy mode (e.g., a mode configured for performing spectroscopic measurements). In embodiments, a spectroscopy mode may comprise an absorbance mode (e.g., a mode configured for performing absorbance measurements). In embodiments, a device configured for operation in a spectroscopy mode may comprise a light source, and may include a light source lens (or lenses) configured to direct light from said light source onto a first optical element mounted on a movable mount (which may be, e.g., a rotatable mount, a translatable mount, or other movable mount) and comprising a diffractive surface (e.g., a grating), and configured so that light diffracted from said first optical element may be reflected by a first mirror to and through a first lens (or first set of lenses). A device configured for use in a spectroscopy mode may comprise, or may be configured to hold or operate with, a sample; for example, such a device may include or be configured to work with a sample holder. Light passing to and through a first lens (or first set of lenses) may be directed onto, and in embodiments may be directed through, a sample (e.g., a sample held in or by a sample holder). A device configured for use in a spectroscopy mode may be configured so that light passing onto, or by, or through a sample may be directed onto a second mirror mounted on a movable mount (which may be, e.g., a rotatable mount, a translatable mount, or other movable mount); such light may be reflected to a reflective surface of a second optical element and thereby reflected and directed to a photodetector for observation, measurement, or analysis.

In embodiments, a device disclosed herein may be configured for operation in a fluorescence mode (e.g., a mode configured for performing fluorescence measurements). In embodiments, a device configured for operation in a fluorescence mode may comprise a light source, and may include a light source lens (or lenses) configured to direct light from said light source onto a first optical element mounted on a movable mount (which may be, e.g., a rotatable mount, a translatable mount, or other movable mount) and comprising a diffractive surface (e.g., a grating), and configured so that light diffracted from said first optical element may be reflected by a first mirror to and through a first lens (or first set of lenses). A device configured for use in a fluorescence mode may comprise, or may be configured to hold or operate with, a sample; for example, such a device may include or be configured to work with a sample holder. Light passing to and through a first lens (or first set of lenses) may be directed onto, and in embodiments may be directed through, a sample (e.g., a sample held in or by a sample holder). A device configured for use in a fluorescence mode may be configured so that light passing onto, or by, or through a sample may be directed onto a second mirror mounted on a movable mount (which may be, e.g., a rotatable mount, a translatable mount, or other movable mount); such light may be reflected to a reflective surface of a second optical element and thereby reflected and directed to a photodetector for observation, measurement, or analysis.

In embodiments, a device disclosed herein may be configured for operation in a luminescence mode (e.g., a mode configured for performing luminescence measurements). In embodiments, a device configured for operation in a luminescence mode may comprise a light source, and may include a light source lens (or lenses) configured to direct light from said light source onto a first optical element mounted on a movable mount (which may be, e.g., a rotatable mount, a translatable mount, or other movable mount) and comprising a diffractive surface (e.g., a grating), and configured so that light diffracted from said first optical element may be reflected by a first mirror to and through a first lens (or first set of lenses). A device configured for use in a luminescence mode may comprise, or may be configured to hold or operate with, a sample; for example, such a device may include or be configured to work with a sample holder. Light passing to and through a first lens (or first set of lenses) may be directed onto, and in embodiments may be directed through, a sample (e.g., a sample held in or by a sample holder). A device configured for use in a luminescence mode may be configured so that light passing onto, or by, or through a sample may be directed onto a second mirror mounted on a movable mount (which may be, e.g., a rotatable mount, a translatable mount, or other movable mount); such light may be reflected to a reflective surface of a second optical element and thereby reflected and directed to a photodetector for observation, measurement, or analysis.

In embodiments, a system may comprise a device disclosed herein. For example, a system having features as disclosed herein may comprise a device which may be configured for operation in a spectroscopy mode, a fluorescence mode, and a luminescence mode. A system may comprise a device disclosed herein, wherein the device can perform spectroscopic observations, measurements and analyses when configured in a spectroscopy mode; can perform fluorescence observations, measurements and analyses when configured in a fluorescence mode; and can perform luminescence observations, measurements and analyses when configured in luminescence mode.

In embodiments, methods disclosed herein may comprise use of a device or system disclosed herein. For example, a method as disclosed herein may comprise use of a device which may be configured for operation in a spectroscopy mode, a fluorescence mode, and a luminescence mode. Methods disclosed herein may comprise use of a device disclosed herein, wherein the device is used to perform spectroscopic observations, measurements and analyses when configured in a spectroscopy mode (including use of a device as disclosed herein for the performance of absorbance measurements); wherein the device is used to perform fluorescence observations, measurements and analyses when configured in a fluorescence mode; and wherein the device is used to perform luminescence observations, measurements and analyses when configured in luminescence mode.

Accordingly, Applicants disclose unified detection devices for fluorometry, luminometry, and spectrometry, comprising:

a first optical element comprising a diffractive surface movably mounted on a first movable mount; a first mirror configured for reflecting light after contact of said light with said grating; a first lens configured for focusing or for collimating light reflected from said first mirror; a second mirror movably mounted on a second movable mount and configured for reflecting light from said first lens; a second optical element movably mounted on a third movable mount, second optical element having a first face and a second face, said first face having a reflective surface configurable to reflect light from said second mirror, and said second face having a diffractive surface configurable to diffract light from said second mirror; a second lens configured for directing light to or onto said second optical element; and a photodetector. In embodiments, may further comprise a sample holder configured to hold a sample for optical observation, measurement, or analysis. In embodiments, a unified detection device as disclosed herein may comprise a sample handling device, or system configured to transport a sample, a sample holder, or both, to a location suitable for observation, measurement, or analysis, e.g., for optical observation, measurement, or analysis. In embodiments, a diffractive surface of a unified detection device as disclosed herein may comprise a grating. In embodiments, at least one of said first movable mount, said second movable mount, and said third movable mount may comprise a translatable, rotatable, or other movable mount. In embodiments, more than one lens may be configured for focusing or for collimating light reflected from said first mirror. In embodiments, more than one lens may be configured for directing light to or onto said second optical element. In embodiments, a unified detection device as disclosed herein may further comprise a light source for illuminating a sample. In embodiments, a light source of a unified detection device may comprise a light source selected from an incandescent lamp, a flash lamp, a laser, a light-emitting diode, and an arc light. In embodiments, a unified detection device as disclosed herein may further comprise one or more of a grating, an aperture, a filter, and a polarizer. In embodiments, a photodetector of a unified detection device as disclosed herein may comprise an optical component selected from a photodiode, a photomultiplier, a charge-coupled device, a spectrophotometer, a camera, and a microscope.

Applicants further disclose systems for fluorometry, luminometry, and spectrometry comprising a unified detection device as disclosed herein; a communication device; and a communication channel operably connecting said device with said communication device. Embodiments of the systems for fluorometry, luminometry, and spectrometry disclosed herein may comprise a unified detection device as disclosed herein; a communication device; a communication channel operably connecting said device with said communication device; and a sample handling device. In embodiments, a system as disclosed herein, or a sample handling device of such a system, may comprise a transport component, device, or system configured to transport a sample, a sample holder, or both, to a location suitable for observation, measurement, or analysis, e.g., for optical observation, measurement, or analysis. In embodiments, a sample handling device may comprise a gantry configured to transport a sample, or may be configured to work in conjunction with a gantry. In embodiments, a fluid handling device or system may comprise a gantry configured to transport a sample, or may be configured to work in conjunction with a gantry. In embodiments, a system for fluorometry, luminometry, and spectrometry may comprise a unified detection device as disclosed herein, and a sample.

Applicants further disclose methods of performing fluorometry, luminometry, and spectrometry. Applicants disclose a method of performing fluorometry, comprising placing a sample in a unified detection device as disclosed herein, and performing a fluorometric observation, measurement, or analysis on said sample. Applicants disclose a method of performing luminometry, comprising placing a sample in a unified detection device as disclosed herein, and performing a luminometric observation, measurement, or analysis on said sample. Applicants disclose a method of performing spectrometry, comprising placing a sample in a unified detection device as disclosed herein, and performing a spectrometric observation, measurement, or analysis on said sample. In embodiments, said spectrometric observation, measurement, or analysis may comprise an absorbance observation, measurement, or analysis.

Applicants disclose methods of performing any two of fluorometry, luminometry, and spectrometry, comprising: placing a sample in a unified detection device as disclosed herein, configuring said unified detection device in a first configuration, wherein said first configuration is selected from a configuration for performing fluorometry, a configuration for performing luminometry, and a configuration for performing spectrometry; performing an observation, measurement, or analysis consistent with said first configuration on said sample while said unified detection device is in said first configuration; configuring said unified detection device in a second configuration, wherein said second configuration is other than said first configuration and is selected from a configuration for performing fluorometry, a configuration for performing luminometry, and a configuration for performing spectrometry; and performing an observation, measurement, or analysis consistent with said second configuration on said sample while said unified detection device is in said second configuration.

Applicants further disclose methods of performing fluorometry, luminometry, and spectrometry, comprising: placing a sample in a unified detection device as disclosed herein; configuring said unified detection device in a first configuration, wherein said first configuration is selected from a configuration for performing fluorometry, a configuration for performing luminometry, and a configuration for performing spectrometry; performing an observation, measurement, or analysis consistent with said first configuration on said sample while said unified detection device is in said first configuration; configuring said unified detection device in a second configuration, wherein said second configuration is other than said first configuration and is selected from a configuration for performing fluorometry, a configuration for performing luminometry, and a configuration for performing spectrometry; performing an observation, measurement, or analysis consistent with said second configuration on said sample while said unified detection device is in said second configuration; configuring said unified detection device in a third configuration, wherein said third configuration is other than said first or said second configuration and is selected from a configuration for performing fluorometry, a configuration for performing luminometry, and a configuration for performing spectrometry; and performing an observation, measurement, or analysis consistent with said third configuration on said sample while said unified detection device is in said third configuration.

In embodiments, a method of performing any two of fluorometry, luminometry, and spectrometry may comprise placing a first sample in said unified detection device for performance of said observation, measurement, or analysis consistent with said first configuration; and placing a second sample in said unified detection device for performance of said observation, measurement, or analysis consistent with said second configuration.

In embodiments, a method of performing fluorometry, luminometry, and spectrometry may comprise placing a first sample in said unified detection device for performance of said observation, measurement, or analysis consistent with said first configuration; placing a second sample in said unified detection device for performance of said observation, measurement, or analysis consistent with said second configuration; and placing a third sample in said unified detection device for performance of said observation, measurement, or analysis consistent with said third configuration.

Applicants further disclose optical elements combining, in a single optical element, optically reflective surfaces and optically dispersive surfaces. A mirror dispersion element as disclosed herein has at least two surfaces, one surface of which includes an optical dispersion element, and another surface of which includes a reflective element. A dispersion element of such mirror dispersion elements may be, e.g., a diffraction grating, or a prism (including a complex prism comprising two or more prism elements), or other optical dispersion element. A reflective element of such mirror dispersion elements may be mirror, e.g., a front surface mirror or a back surface mirror, and may include both a front surface mirror and a back surface mirror. In embodiments, a mirror dispersion element may be configured so as to be able to present an optical dispersion element to impinging light in one configuration and to present a reflective element to impinging light in another configuration. For example, a mirror dispersion element may be mounted on a movable mount (which may be, e.g., a rotatable mount, a translatable mount, or other movable mount), so that the mirror dispersion element may present an optical dispersion element such as a diffraction grating or a prism to impinging light in a first configuration, and, following movement (e.g., rotation or translation) of the movable mount, to present a reflective element to impinging light in a second configuration.

Applicants further disclose optical devices comprising such mirror dispersion elements. Optical devices comprising mirror dispersion elements as disclosed herein may be used for optical measurements, including analysis of samples, such as biological samples, by optical means. Optical devices comprising mirror dispersion elements as disclosed herein may be used to perform spectroscopic (absorbance) measurements, to perform fluorescence measurements, and to perform luminescence measurements.

Applicants further disclose systems including optical devices comprising such mirror dispersion elements. Systems including such mirror dispersion elements as disclosed herein, such as systems including optical devices comprising mirror dispersion elements may be used for optical measurements, including analysis of samples, such as biological samples, by optical means. Systems including mirror dispersion elements as disclosed herein, including systems including optical devices comprising mirror dispersion elements may be used to perform spectroscopic (absorbance) measurements, to perform fluorescence measurements, and to perform luminescence measurements.

The devices, systems, and methods disclosed herein provide multiple optical capabilities in a single device or system. Devices disclosed herein are capable of performing spectroscopic, fluorescence, and luminescence observations, measurements and analyses; systems including these devices are also capable of performing all such optical observations, measurements and analyses. Provision of such multiple capabilities in a single device or in a single system may eliminate the need to move or load a sample in multiple devices when subjecting a sample to multiple analyses; thus, devices, systems and methods disclosed herein may provide greater accuracy, precision, and speed of sample analysis. Eliminating the need to load a sample on multiple devices for multiple analyses may reduce degradation of a sample where the time to perform multiple analyses is reduced as compared to prior devices, systems, or methods requiring use of multiple devices or systems. Provision of such multiple capabilities in a single device or in a single system may thus simplify and streamline the observation, measurement, and analysis of samples. Provision of such multiple capabilities in a single device or in a single system may reduce the time required, and may reduce the cost of, the observation, measurement, and analysis of samples. Providing such multiple capabilities in a single device or in a single system may simplify the design and operation of machines and systems for observing, measuring, and analyzing samples. Thus, devices, systems and methods disclosed herein provide greater ease, accuracy, precision, and speed of sample analysis while reducing the complexity and cost of such analyses. Accordingly, the devices, systems, and methods disclosed herein provide advantages over prior devices, systems, and methods.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1A:
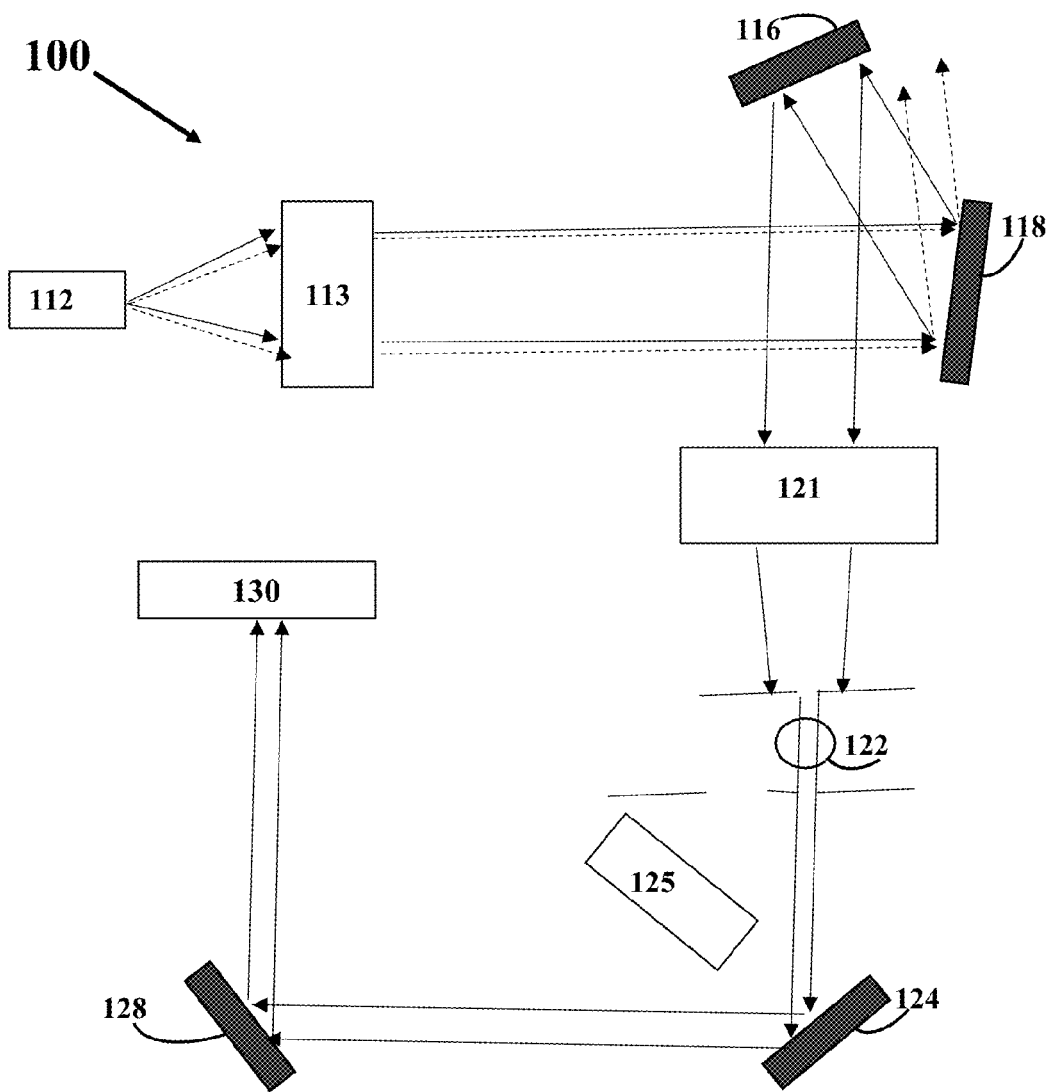
FIG. 1A illustrates elements of a device in a configuration for use in spectroscopy (absorbance) mode.

Description and disclosure which may aid in understanding the full extent and advantages of the devices, systems, and methods disclosed herein may be found, for example, in U.S. Pat. No. 7,888,125; U.S. Pat. No. 8,088,593; U.S. Pat. No. 8,158,430; U.S. Pat. No. 8,380,541; U.S. patent application Ser. No. 13/951,063, filed Jul. 25, 2013; U.S. patent application Ser. No. 13/951,449, filed Jul. 25, 2013; U.S. patent application Ser. No. 13/769,820, filed Feb. 18, 2013; U.S. patent application Ser. No. 13/769,798, filed Feb. 18, 2013; U.S. Patent Application Ser. No. 61/802,194, filed Mar. 15, 2013; U.S. patent application Ser. No. 13/769,779, filed Feb. 18, 2013; U.S. patent application Ser. No. 13/244,947 filed Sep. 26, 2011; International Patent Application PCT/US2012/57155, filed Sep. 25, 2012; U.S. patent application Ser. No. 13/244,946, filed Sep. 26, 2011; U.S. Patent Application Ser. 61/801,996, filed Mar. 15, 2913; U.S. patent application Ser. No. 13/244,949, filed Sep. 26, 2011; and U.S. Patent Application Ser. No. 61/673,245, filed Sep. 26, 2011, the disclosures of which patents and patent applications are all hereby incorporated by reference in their entireties. The publications discussed or cited herein are provided solely for their disclosure prior to the filing date of the present application. Nothing herein is to be construed as an admission that the present invention is not entitled to antedate such publication by virtue of prior invention.

In this specification and in the claims which follow, reference will be made to a number of terms which shall be defined to have the following meanings:

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like.

As used in the description herein and throughout the claims that follow, the meaning of "or" includes "and/or" (i.e., "or" includes both the conjunctive and disjunctive) unless explicitly stated otherwise, or unless the context expressly dictates otherwise.

As used in the description herein and throughout the claims that follow, the meaning of "in" includes "in" and "on" unless the context clearly dictates otherwise.

References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a urine sample, a tissue sample (e.g., a biopsy sample or a tissue slice), or other biological sample, however obtained or prepared. A blood sample may be, for example, obtained from a finger-stick, or from venipuncture, or an arterial blood sample, and may be whole blood, serum, plasma, or other blood sample. Further examples of samples include, without limitation, a water sample, a soil sample, a food sample, an air sample; or other sample (e.g., a stool sample, a throat swab, a nasal swab or nasopharyngeal wash, a sample of saliva, urine, tears, gastric fluid, spinal fluid, mucus, sweat, earwax, oil, glandular secretion, cerebral spinal fluid, tissue, semen, cervical fluid, vaginal fluid, synovial fluid, breath, hair, finger nails, skin, biopsy, placental fluid, amniotic fluid, cord blood, lymphatic fluids, cavity fluids, sputum, mucus, pus, microbiota, meconium, breast milk or other secretion or excretion).

Thus, as used herein, a "sample" includes a portion of a blood, urine, or other biological sample, may be of any suitable size or volume, and is preferably of small size or volume. In some embodiments of the systems, assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, an "optical detector" detects electromagnetic radiation (e.g., light, including light in the visible spectrum and light of wavelengths typically not visible to human observers (including without limitation infrared, ultraviolet, and other wavelengths of light)). An optical detector may detect an image or be used with an image, or may detect light intensity irrespective of an image, or both. An optical detector may detect, or measure, light intensity. Some optical detectors may be sensitive to, or restricted to, detecting or measuring a particular wavelength or range of wavelengths. For example, optical detectors may include, for example, photodiodes (including, e.g., avalanche photodiodes), photomultipliers, charge-coupled devices, spectrophotometers, cameras, microscopes, and other devices (e.g., phototransistors, phototubes, photoresistors, photovoltaics, and other light-sensitive components, elements, and devices, embodying any suitable technology (including, e.g., complementary metal oxide semiconductor (CMOS), N-type metal oxide semiconductor (NMOS), thin-film transistor (TFT), and other technologies)) which detect light or measure light intensity (of a single wavelength, of multiple wavelengths, or of a range, or ranges, of wavelengths of light), form an image, or both.

As used herein, the term "microscopy" refers to optical methods which involve imaging a sample, and which typically involve magnification, enlargement, or other techniques in order to provide a magnified image of a sample or portion of a sample. Microscopy may involve one or more of fluorescence microscopy, dark field microscopy, bright field microscopy, interference contrast microscopy, phase contrast microscopy, and other microscopy methods to image, observe, or measure one or more portions of a sample or attributes of a sample or portion thereof. Such methods may, e.g., provide morphometric information regarding cells, particles, or other portions or constituents of a sample. Such information may be measured quantitatively. In some embodiments, for quantitative microscopy, a sample is analyzed by two or more of quantitative fluorescence microscopy, quantitative dark field microscopy, quantitative bright field microscopy, and quantitative phase contrast microscopy. Quantitative microscopy may include use of image analysis techniques and/or statistical learning and classification methods to process images obtained by microscopy.

A sample to be analyzed, e.g., by optical or imaging means, may be held in a sample holder for analysis. For example, a cuvette may serve as such a sample holder. Other sample holding devices may also be used in place of or in combination with a cuvette. For example, a microscope slide may serve as a sample holder; a tube may serve as a sample holder; a clamp may serve as a sample holder; a receptacle may serve as a sample holder; a surface may serve as a sample holder; or other object, implement, or device may serve to hold a sample, or portion thereof, for optical observation, measurement, or analysis.

In embodiments, devices having features as disclosed herein may include the following elements:

A) a light source or multiple light sources. Suitable light sources include, for example, Xenon or other flash lamps; incandescent lamps; lasers; light-emitting diodes; arc lights; and other light sources or combinations of light sources which provide a single wavelength of light, or a narrow range of wavelengths of light (a narrowband source), or a wide range of wavelengths of light (a broadband light source). A narrowband or broadband light source may be used to provide a narrower range of wavelengths, or to provide a single wavelength, by use of filters, prisms, gratings, or other optical elements;

B) a lens or lenses for collimating, collecting and focusing light;

C) a mirror or mirrors for collimating, collecting and focusing light;

D) optical elements for wavelength selectivity, including filters, polarizers, prisms, dispersion elements and diffraction systems, pinholes, slits, surface coatings, surface textures or features, or other optical elements which may be used to select or affect the wavelength(s) of light transmitted, reflected, or diffracted in the device. In embodiments, such optical elements for wavelength selectivity may be mounted on rotatable, translatable, or otherwise movable mounts, effective that the optical elements may be positioned for use as desired. Such positioning includes providing for operational and non-operational positions and modes (e.g., positioning of an optical element in a light path for use in diffracting light when desired, and positioning an optical element outside of a light path (or positioning it so light diffracted by the optical element does not affect or impact the measurement) when use of such optical element is not desired);

E) an optical detector (which may be one or more of any suitable photodetector, including, e.g., a photomultiplier tube (PMT), a photodiode, a charge-coupled device (CCD), a spectrophotometer, a camera, a microscope, or other photodetector) to act as a transducer effective to convert the received optical signal into an electrical signal. A PMT or other optical detector may be used in counting or in analog mode, or both, depending on the signal to noise requirements of the application. In embodiments, amplifiers, electronic filters, analog-to-digital converters, multiplexers, and other circuit elements and devices may be connected to and may be used with an optical detector.

As discussed above, optical elements for wavelength selectivity (element D) may be mounted on rotatable, translatable, or otherwise movable mounts, in order that, for example, an excitation path dispersion element can be moved so as to select the wavelength that passes through the sample; or that an emission path dispersion element can be moved so as to select which wavelength is measured by the photodetector. In embodiments, an excitation path dispersion element may be, for example, a diffraction grating. For example, such movement may include rotation (e.g., around an axle or other mount), transverse motion (e.g., along a direction substantially perpendicular to a light path), longitudinal motion (e.g., along a direction substantially parallel to a light path), other lateral motion, or a combination thereof. Such movement may be useful to make minor adjustments or corrections in position or orientation of the optical element; may be useful to make substantial changes in the position or orientation of the optical element (e.g., movement of the optical element into, or out of, an optical path); or combinations thereof. In embodiments, an emission path dispersion element may be coupled to a mirror (e.g., a mirror mounted on the reverse side of the emission path dispersion element), so that the emission path dispersion element may be rotated, translated, or otherwise moved out of the light path, and the mirror used to redirect light to the photodetector.

Similarly, and without limitation, other elements may be mounted on rotatable, translatable, or otherwise movable mounts, in order that, for example, a lens, or filter, or prism, slit, pin-hole, or other optical element can be moved in order to adjust the placement of that element in the light path, or to remove the element from the light path. For example, such movement may include rotation (e.g., around an axle or other mount), and may include translation, where translation may include i) transverse motion (e.g., along a direction substantially perpendicular to a light path), ii) longitudinal motion (e.g., along a direction substantially parallel to a light path), iii) other lateral motion, or a combination thereof. Such movement may be useful to make minor adjustments or corrections in position or orientation of the optical element; may be useful to make substantial changes in the position or orientation of the optical element (e.g., movement of the optical element into, or out of, an optical path); or combinations thereof.

As discussed above, an optical detector may be used in photon counting mode (counting mode) or in analog mode. An optical detector used in analog mode provides an analog (e.g., voltage) output; an optical detector used in counting mode provides a digital output. The counting mode can be implemented either in hardware (e.g., on-board the optical detector, or in hardware connected to the optical detector) or externally through a software algorithm. In embodiments, an optical detector may be configured for use in both counting mode and analog mode, and may be configured to switch between these modes as needed for a particular application, observation, measurement, or analysis. For example, a PMT used for spectrophotometry applications (where sensitivity is typically not a significant issue) may provide usable output signals either as photon numbers (in counting mode) or as voltages (in analog mode). However, for other applications where the signal to be detected may be a low-intensity light signal, e.g., luminescence measurements, a PMT may be advantageously used in analog mode to provide high sensitivity even at low light levels. In other applications (e.g., fluorometric measurements) a PMT may be used in either counting mode or analog mode, as the application, expected light intensity, or other considerations may determine.

Thus, in embodiments, a PMT may be used in either counting or analog modes. In embodiments, a PMT may be used in photon-counting mode which enumerates photon counts detected by the PMT. However, a PMT used in an analog mode may also provide photon counts, e.g., where a quantization algorithm implemented in software is used to provide photon counts from analog signals from the PMT.

In embodiments, a PMT may be used in analog mode, which provides a high signal-to-noise ratio, and allows precise detection of very small photon counts. Despite possible non-linearity of PMT response at low light levels, such use of a PMT in analog mode provides an advantage as compared to use of a PMT in photon-counting mode, for example, since use of a PMT in counting mode typically requires application of a minimum threshold. Such a minimum threshold (e.g., as used in counting mode) may have the effect of reducing sensitivity to low intensity signals, since, e.g., signals near or below the threshold may be lost or miscounted.

An optical detector other than a PMT (e.g., a photodiode, a CCD, or other optical detector) may be configured for use in both a digital (e.g., counting) mode and an analog mode, and may be configured to switch between these modes as needed for a particular application or a particular observation, measurement, or analysis.

As discussed above, devices disclosed herein include all elements needed for use in each of at least three configurations (also termed modes): spectroscopy mode, fluorescence mode, and luminescence mode. A device as disclosed herein may be used to perform spectroscopic observations, measurements, and analyses on a sample or samples when used in spectroscopy mode; such spectroscopic observations, measurements, and analyses may include absorbance observations, measurements, and analyses. A device as disclosed herein may be used to perform fluorescence observations, measurements, and analyses on a sample or samples when used in fluorescence mode. A device as disclosed herein may be used to perform luminescence observations, measurements, and analyses on a sample or samples when used in luminescence mode.

In embodiments, devices as disclosed herein may further include other elements which aid in, or may be used in conjunction with, the performance of optical observations, measurements, and analyses. Such other elements may include, without limitation, mechanical elements, for handling and positioning samples, sample holders, and other containers, implements and system elements; fluidic elements, for providing, transporting, and removing fluids as necessary for the observations, measurements, and analyses; and other elements.

Systems are disclosed which include devices which include all elements needed for use in each of at least the three modes: spectroscopy mode, fluorescence mode, and luminescence mode. In embodiments, systems may further include, without limitation, communication elements, for communicating (raw or processed) output and results of optical observations, measurements, and analyses; mechanical elements, for handling and positioning samples, sample holders, and other containers, implements and system elements; fluidic elements, for providing, transporting, and removing fluids as necessary for the observations, measurements, and analyses; and other elements.

Further elements which may be included in devices and systems disclosed herein, or which may be used in conjunction with devices and systems disclosed herein, include, for example, a fluid handling device or system that is configured to transport a sample, a sample holder, or other object or container to the measuring area. Further elements which may be included in devices and systems disclosed herein, or which may be used in conjunction with devices and systems disclosed herein, include, for example, a pipette and gantry system that prepares the samples, or transports them to the measuring area. Devices and systems disclosed herein may include, or may be used in conjunction with, identification elements, devices, or systems for identifying and tracking samples (e.g., bar codes and bar code readers; quick response (QR) code elements and readers; near field communication (NFC) elements and readers; radiofrequency identification (RFID) elements and readers; and other such identification elements and readers).

As illustrated in the figures, a unified detection device capable of performing fluorometry, luminometry, and spectrometry as disclosed herein may include the following elements: a light source (e.g., a lamp, light-emitting diode, fluorescent bulb, or other light source) 112; optics 113 for beam collimation and beam-shaping, such as, e.g., a light source lens 114; a first mirror 116 (which may be fixed or may be movable); a first optical element 118 (mounted on a movable, e.g., rotatable or translatable mount); optics 121 for focusing light toward or onto an aperture, sample, or both, such as, e.g., a first lens or first set of lenses (e.g., 120A and 120B) for focusing or collimating light (e.g., onto or through an optional aperture 144, such as a pin-hole, a slit, a slot, or other open or transparent passage providing a light path); a second mirror 124 (which may be fixed or may be movable); optics 125 for collecting, collimating, or focusing light from a sample, such as, e.g., a second lens or set of lenses 126 (which may be fixed or may be movable) for collimating light (e.g., a collection lens); a second optical element 128 having a mirror face and a diffraction face (e.g., a grating) mounted on a movable, e.g., rotatable or translatable, mount); and a photodetector 130 (e.g., a photomultiplier (PMT), a charge-coupled device (CCD), a photodiode, or other optical detector). A sample 122 may be placed in the light path of a unified detection device as disclosed herein for observation, measurement, and analysis. A sample 122 may be held in a sample holder, receptacle, channel, clamp, or otherwise located at a location suitable for such observation, measurement, and analysis.

It will be understood that a unified detection device capable of performing fluorometry, luminometry, and spectrometry as disclosed herein may use only some, or may use all, of the above-mentioned elements and components depending on the particular desired use or configuration. For example, among multiple elements and components used, a light source 112; a light source lens 114; a first mirror 116; a first optical element 118; a first lens or first set of lenses (e.g., 120A and 120B); and a photodetector 130 may be utilized when a unified detection device capable of performing fluorometry, luminometry, and spectrometry as disclosed herein is used to perform spectrometric (including absorbance) observations, measurements, or analysis. For further example, among multiple elements and components used, a light source 112; a light source lens 114; a first mirror 116; a first optical element 118; a first lens or first set of lenses (e.g., 120A and 120B); and a photodetector 130 may be utilized when a unified detection device capable of performing fluorometry, luminometry, and spectrometry as disclosed herein is used to perform fluorometric observations, measurements, or analysis. For further example, among multiple elements and components used, a collection mirror 124; a collection lens 126; a second optical element 128; and a photodetector 130 may be utilized when a unified detection device capable of performing fluorometry, luminometry, and spectrometry as disclosed herein is used to perform luminometric observations, measurements, or analysis.

In embodiments, a first optical element 118 may comprise a diffraction element, such as a grating; in embodiments, a first optical element 118 may comprise a grating (or other dispersion element) and a mirror. A first optical element 118 may be mounted on a rotatable, translatable, or otherwise adjustable mount which allows positioning first optical element 118 in a position and orientation suitable for directing diffracted or reflected light onto first mirror 116. In embodiments, a second lens or second set of lenses 120A and 120B may be configured to focus light onto a sample 122, or to collimate light onto a sample 122 (e.g., a lens or lenses 120A may be configured to focus or collimate light along light paths closer to the light source 112 than the sample 122); and may be configured to focus or collimate light leaving the sample 122 (e.g., a lens or lenses 120B may be configured to focus or collimate light along light paths closer to the photodetector 130 than the sample 122). A second mirror 124 may be mounted on a rotatable mount, or a translatable mount, or an otherwise adjustable mount which allows positioning second mirror 124 in a position and orientation suitable for directing incident light onto second optical element 128, or away from second optical element 128 as needed in a particular configuration. A second optical element 128 may be mounted on a rotatable, translatable, or otherwise movable mount which allows positioning second optical element 128 in a position and orientation suitable for directing diffracted or reflected light onto photodetector 130. A second optical element 128 may have both a diffractive face and a reflective face, which may be the same face or which may be different faces. Where a second optical element 128 has different faces (e.g., a reflective face and a diffractive face) the second optical element 128 may be configured in a reflective position and orientation suitable for reflecting light onto photodetector 130, and may be configured in at least two different configurations: i) a reflective position and orientation suitable for reflecting light onto photodetector 130, and ii) a in a diffractive position and orientation suitable for diffracting light onto photodetector 130.

In embodiments, a mirror, lens, optical element, or other component of a unified detection device or system may be mounted so as to be rotatable, translatable, or otherwise movable. Such movable mounting configurations may utilize a rotor; an axle; a pivot; a hinge; a bearing; a belt; a slide or way; a cam; or other movable (including slidable) part. Such movable mounting configurations may include a motor (including a stepping motor); a screw or other threaded component; a piston; a piezoelectric actuator or positioner; a pneumatic or hydraulic positioner or drive; or other motive element. Such rotatable, translatable, or otherwise adjustable mounting configurations may include tubing, wiring, springs, tensioners, gaskets, attachment elements such as clamps, bolts, glue, fasteners, friction plates, supports, and other mechanical and structural elements.

It will be understood that a unified detection device capable of performing fluorometry, luminometry, and spectrometry as disclosed herein may include further components, elements, and capabilities as well, including additional components, elements and capabilities named above and including components, elements and capabilities other than those named above. For example, in embodiments, a unified detection device capable of performing fluorometry, luminometry, and spectrometry as disclosed herein may include a communication component, effective to communicate with a user, an external device, a network, or other device or system. In embodiments, a unified detection device capable of performing fluorometry, luminometry, and spectrometry as disclosed herein may include a communication link or channel, for use in communicating with a user, an external device, a network, or other device or system. In embodiments, a unified detection device capable of performing fluorometry, luminometry, and spectrometry as disclosed herein may include a sample handling component, for use in loading, transporting, orienting, securing, maintaining, removing, or otherwise aiding or effecting the positioning and disposition of a sample prior to, during, or after observation, measurement, or analysis by a unified detection device.

In addition, it will be understood that a system for performing fluorometry, luminometry, and spectrometry (the system comprising a unified detection device capable of performing fluorometry, luminometry, and spectrometry as disclosed herein) may include further components, elements, devices, and capabilities as well, including additional components, elements and capabilities named above and including components, elements and capabilities other than those named above. Numbers displayed in FIGS. 1A and 1B indicating a particular component, element, or feature may also refer to corresponding components, elements, or features displayed in FIGS. 2A and 2B, and in FIGS. 3A and 3B. Similarly, text in FIGS. 1A, 1B, 2A, 2B, 3A, and 3B describing components, elements, or features displayed in those figures also serves to describe corresponding components, elements, or features displayed in other figures.

Figure 5A:
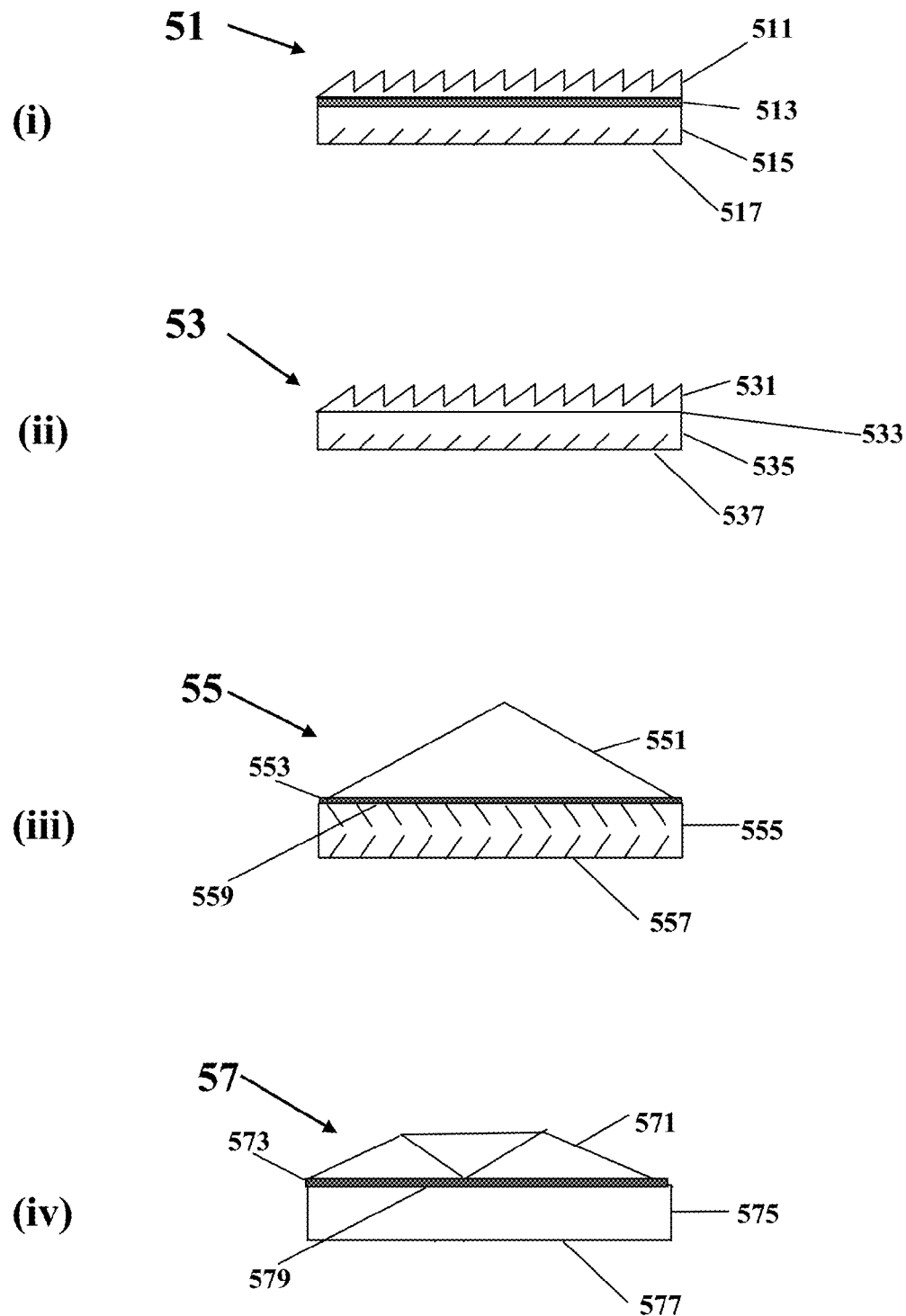
FIG. 5A illustrates embodiments of mirror dispersion elements as disclosed herein, having reflective elements on one face and optically dispersive elements on another face.
Figure 5B:
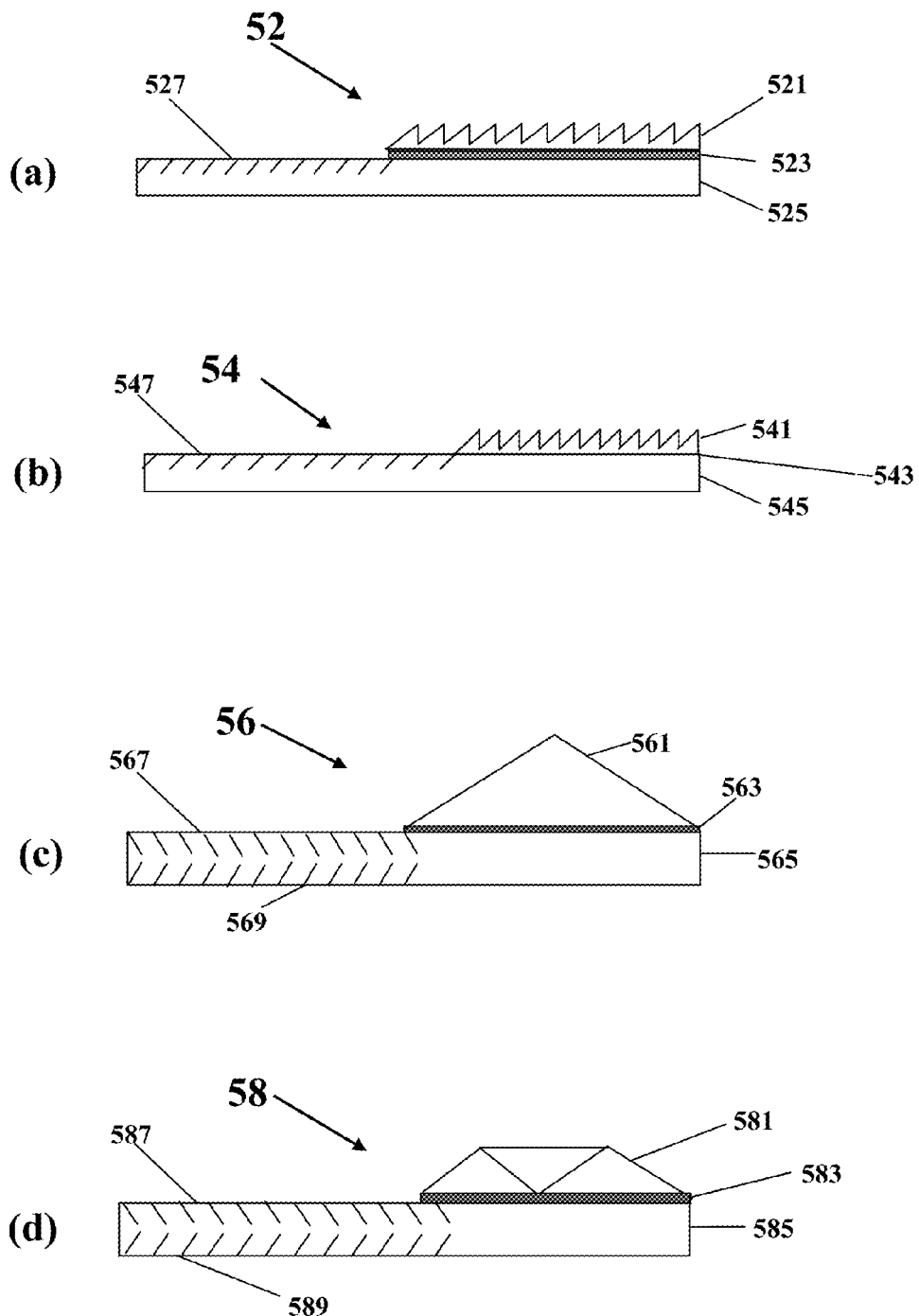
FIG. 5B illustrates embodiments of mirror dispersion elements as disclosed herein, having reflective elements and optically dispersive elements on the same face of the mirror dispersion element.

In FIGS. 1A, 1B, 2A, and 2B, light from a light source 112 (e.g., a lamp, a fluorescent light, a light-emitting diode, a laser, or other light source) is produced and directed through lens or lenses 114, providing illumination (via optical elements, mirrors, lenses, apertures, or other elements along a light path) to the sample 122. Such light illuminates sample 122, and may pass through sample 122; may cause fluorescent or other emission of light from sample 122; may be scattered or diffracted by sample 122; may be reflected by sample 122; or combinations thereof. Optical elements 128 are shown in FIGS. 1A, 1B, 2A, 2B, 3A, 3B, and 5; an optical element 128 may be configured to have at least two sides, of which one side has a mirror surface and another side has an optically dispersive surface (e.g., a dispersion element such as a diffraction grating, a prism, or other optically dispersive element). Examples of several embodiments of such an optical element 128 are shown in FIGS. 5A and 5B.

Figure 1B:
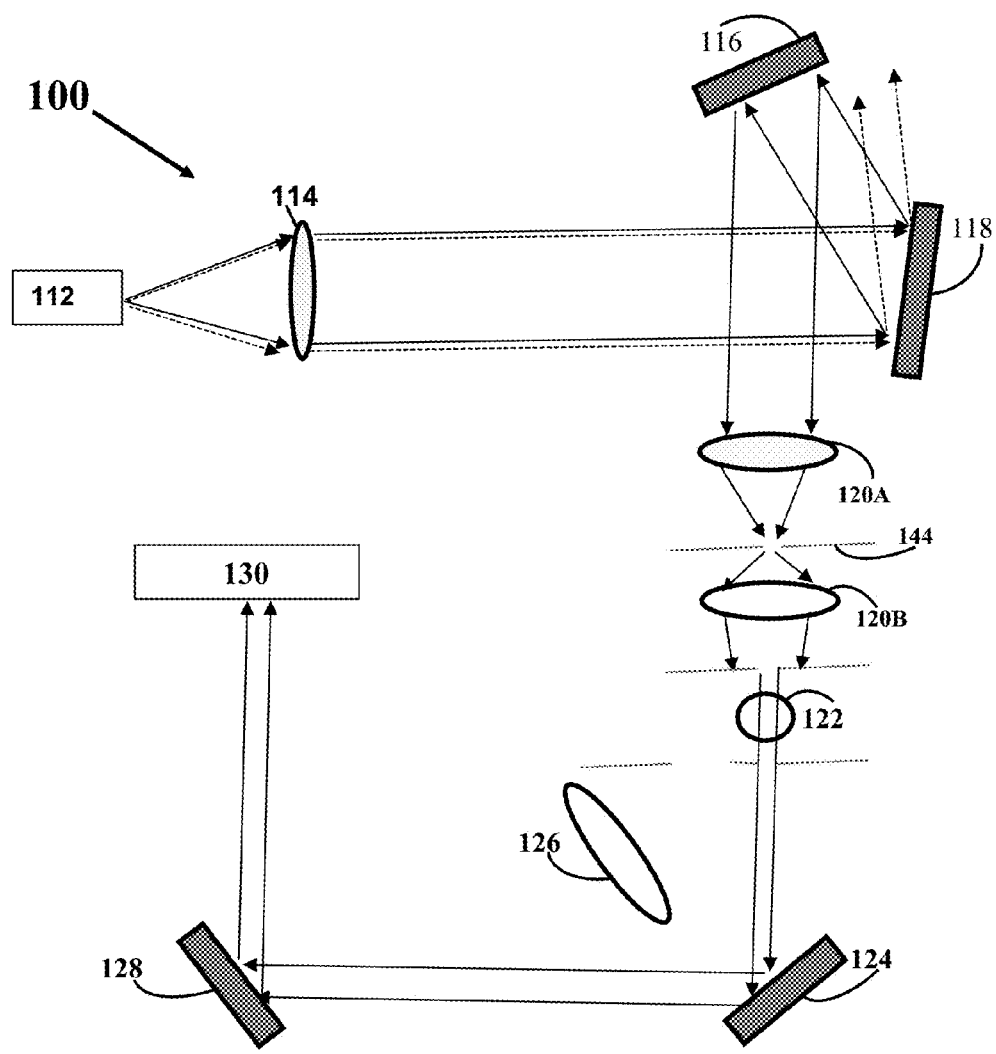
FIG. 1B illustrates elements of an embodiment of a device in a configuration for use in spectroscopy (absorbance) mode.

FIGS. 1A and 1B provide illustrations of embodiments of a device configuration (of a unified detection device capable of performing fluorometry, luminometry, and spectrometry as disclosed herein) for use in spectroscopy (absorbance) mode. FIGS. 1A and 1B illustrate embodiments in which light from light source 112 is collimated and shaped by beam collimation and shaping optics 113 (FIG. 1A) such as lens 114 (FIG. 1B). Further along, following reflection, diffraction, or both, by optical elements 116 and 118, the light passes through focusing optics 121 (FIG. 1A) such as, e.g., lenses 120A and 120B and aperture 144 (FIG. 1B) and is directed to the sample 122. Also shown are collection optics 125 (in FIG. 1A) such as collection lens 126 (in FIG. 1B), which are not in the light path in the configuration shown in FIGS. 1A and 1B. A unified detection device capable of performing fluorometry, luminometry, and spectrometry as disclosed herein configured in Spectroscopy mode 100 is illustrated in FIGS. 1A and 1B, wherein:

A) the excitation path grating (first optical element 118) is rotated (or otherwise moved) to select the wavelength or wavelengths of interest. As illustrated in FIGS. 1A and 1B, light source 112 provides multiple wavelengths of light (exemplified as two sequences of arrows; the upper arrows of the pairs signifying one wavelength (indicated by solid lines) and the lower arrows of the pairs signifying another wavelength (indicated by dashed lines). As illustrated in FIGS. 1A and 1B, the upper arrows of the pairs (e.g., red light signified by solid lines) are diffracted towards the first mirror 116 by first optical element 118, while the lower arrows of the pairs (e.g., green light, signified by dashed lines) are diffracted away from first mirror 116 by first optical element 118.

B) the selected wavelength or wavelengths of interest is (or are) reflected by first mirror 116 and then transmitted to and through the sample 122 (e.g., via focusing optics 121 (FIG. 1A) such as a lens or lenses 120A and 120B (FIG. 1B) and aperture 144). The path of the selected wavelength or wavelengths are shown by the single lines of arrows oriented vertically in the figure between first mirror 116 and to and past sample 122.

C) the collection mirror 124 is used direct the transmitted light to the second optical element 128 (configured as a secondary mirror: i.e., a reflective face of second optical element 128 is positioned in an orientation effective for it to interact with and reflect incident light directed to it from collection mirror 124), which in turn directs light to the photodetector 130. The path of the selected wavelength or wavelengths of light after reflection by collection mirror 124 are shown by the single lines of arrows oriented horizontally in the figure between collection mirror 124 and to second optical element 128 (which may be, e.g., a mirror, a diffraction grating, or other optical element). In embodiments, optical element 128 has both a mirror side and a dispersion side (e.g., a dispersion side may be or include a diffraction grating).

D) in embodiments, a diffractive face (e.g., an emission path grating) of second optical element 128 may be used in place of a reflective face (e.g., a secondary mirror configuration) of second optical element 128 for further wavelength resolution (i.e., a diffractive face of second optical element 128 may be positioned in an orientation effective for it to interact with and diffract incident light directed to it from collection mirror 124). The paths of the light after reflection by second optical element 128 are shown by the single lines of arrows oriented vertically in the figure between second optical element 128 and photodetector 130.

An optical element 128 may have at least two sides, including a mirror surface side and a side having an optically dispersive surface such as a diffraction grating or a prism. In the spectroscopy (absorbance) mode as illustrated in FIGS. 1A and 1B, either the mirror side of optical element 128 or the dispersion side of optical element 128 may be used. Using the dispersion side provides further wavelength selectivity.

Figure 2A:
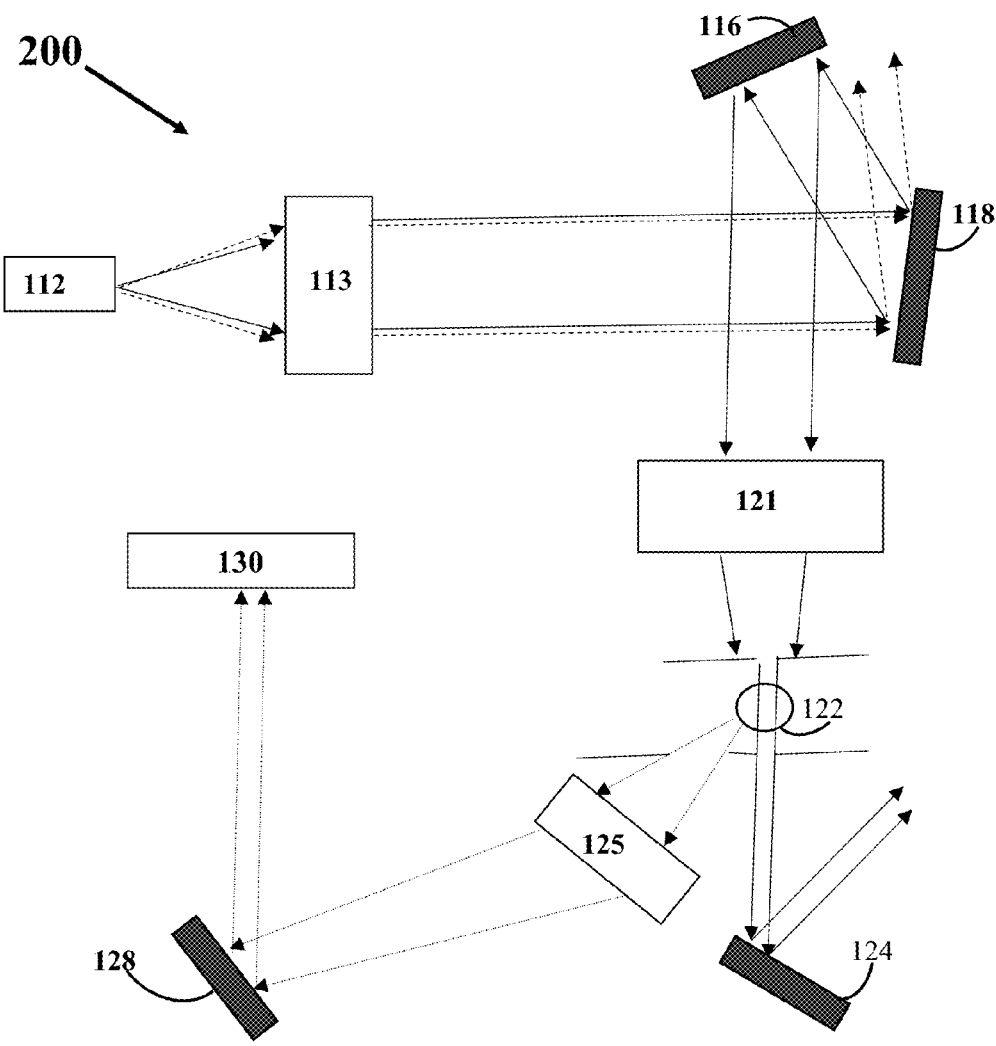
FIG. 2A illustrates elements of a device in a configuration for use in fluorescence mode.
Figure 2B:
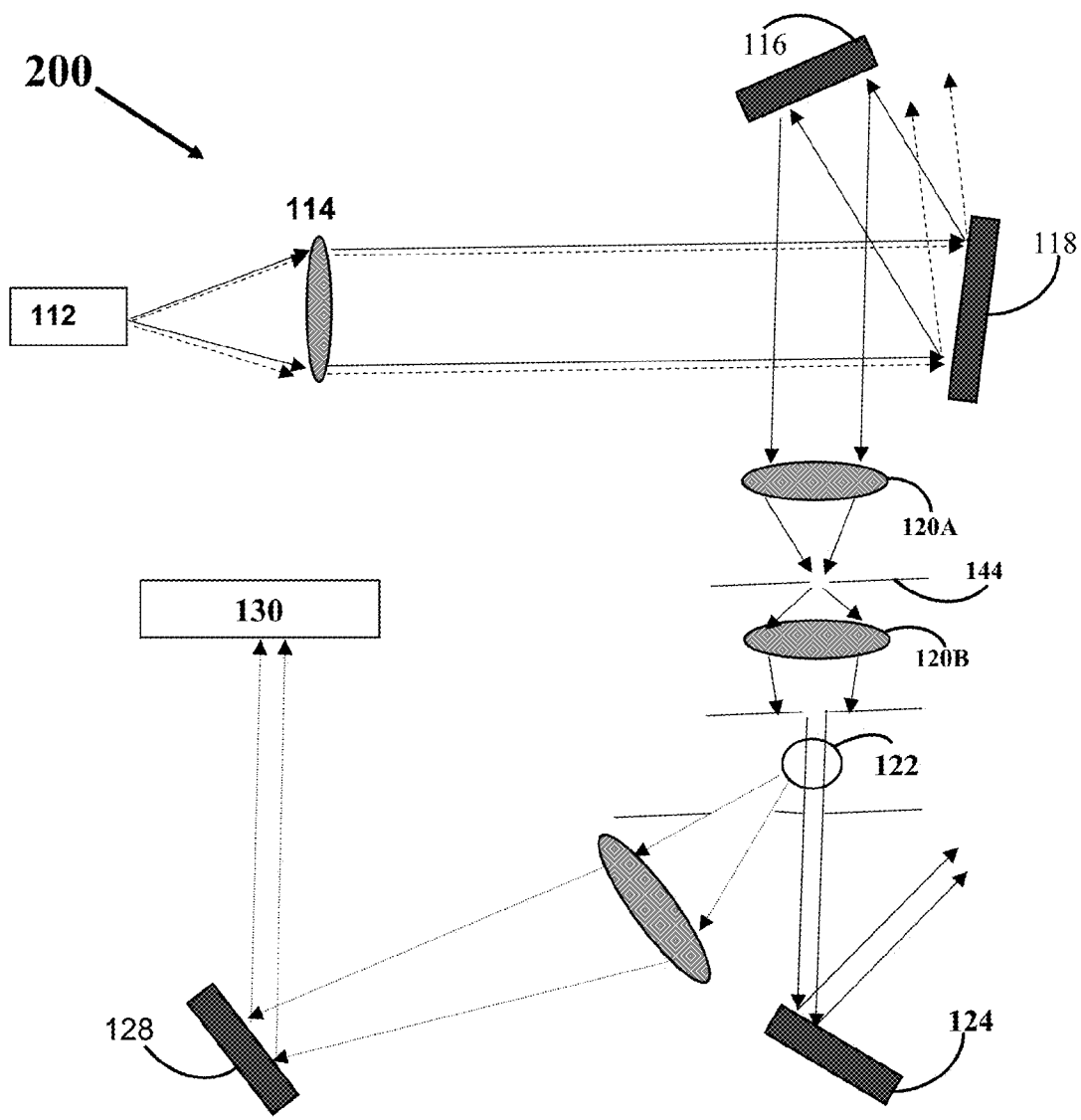
FIG. 2B illustrates elements of a device in a configuration for use in fluorescence mode.

FIGS. 2A and 2B provide illustrations of embodiments of a device configuration (of a unified detection device capable of performing fluorometry, luminometry, and spectrometry as disclosed herein) for use in fluorescence mode. In fluorescence mode 200 as illustrated in FIGS. 2A and 2B:

A) The excitation path grating (first optical element 118) is rotated (or otherwise moved) to select the wavelength or wavelengths of interest, which is (or are) reflected from first mirror 116 and transmitted to and through the sample 122

(e.g., via focusing optics 121 (FIG. 2A) or lens or lenses 120A and 120B (FIG. 2B) and aperture 144). As illustrated in FIGS. 2A and 2B, light source 112 provides multiple wavelengths of light (exemplified as two sequences of arrows; the upper arrows of the pairs signifying one wavelength (e.g., as a solid line) and the lower arrows of the pairs signifying another wavelength (e.g., as a dashed line). As illustrated in FIGS. 2A and 2B, the upper arrows of the pairs (signifying, e.g., blue) are diffracted towards the first mirror 116 by first optical element 118, while the lower arrows of the pairs (signifying, e.g., green) are diffracted away from first mirror 116 by first optical element 118. The paths of the selected wavelength or wavelengths are shown by the single lines of arrows oriented vertically in the figure between first mirror 116 and to and past sample 122.

B) Collection optics 125 (FIG. 2A) such as an off-axis collection lens 126 (shown in FIG. 2B) collects the fluorescence light emitted by the sample 122, and directs it to the diffractive face of second optical element 128 (i.e., second optical element 128 is positioned in an orientation effective for a diffractive face (e.g., an emission path grating) to interact with and diffract incident light directed to it from collection optics 125 (such as a collection lens 126)). Collection optics 125 (e.g., a collection lens 126) collimates fluorescent light from the sample 122. The paths of the fluorescence light emitted by the sample 122 are shown by the single lines of arrows oriented towards collection optics 125 (such as a collection lens 126) and then are directed by collection optics 125 (such as a collection lens 126) towards second optical element 128.

C) the second optical element 128 (i.e., a diffractive face (e.g., emission path grating) of second optical element 128) is rotated (or otherwise moved) to measure light at the wavelength of interest by directing the light to photodetector 130. The paths of the fluorescence light emitted by the sample 122 after its direction by second optical element 128 is shown by the single lines of arrows oriented towards photodetector 130. In fluorescence mode, as illustrated in FIGS. 2A and 2B, the dispersion side of an optical element 128 is used.

D) the collection mirror 124 is rotated (or otherwise moved) so that the excitation light (i.e., light that passes by or through the sample from light source 112) is prevented from reaching the photodetector 130 (e.g., collection mirror 124 is positioned so that excitation light is directed away from the detector). Light paths prevented from reaching the photodetector 130 are shown angling away from collection mirror 124 in a partially vertical direction (FIGS. 2A and 2B).

Figure 3A:
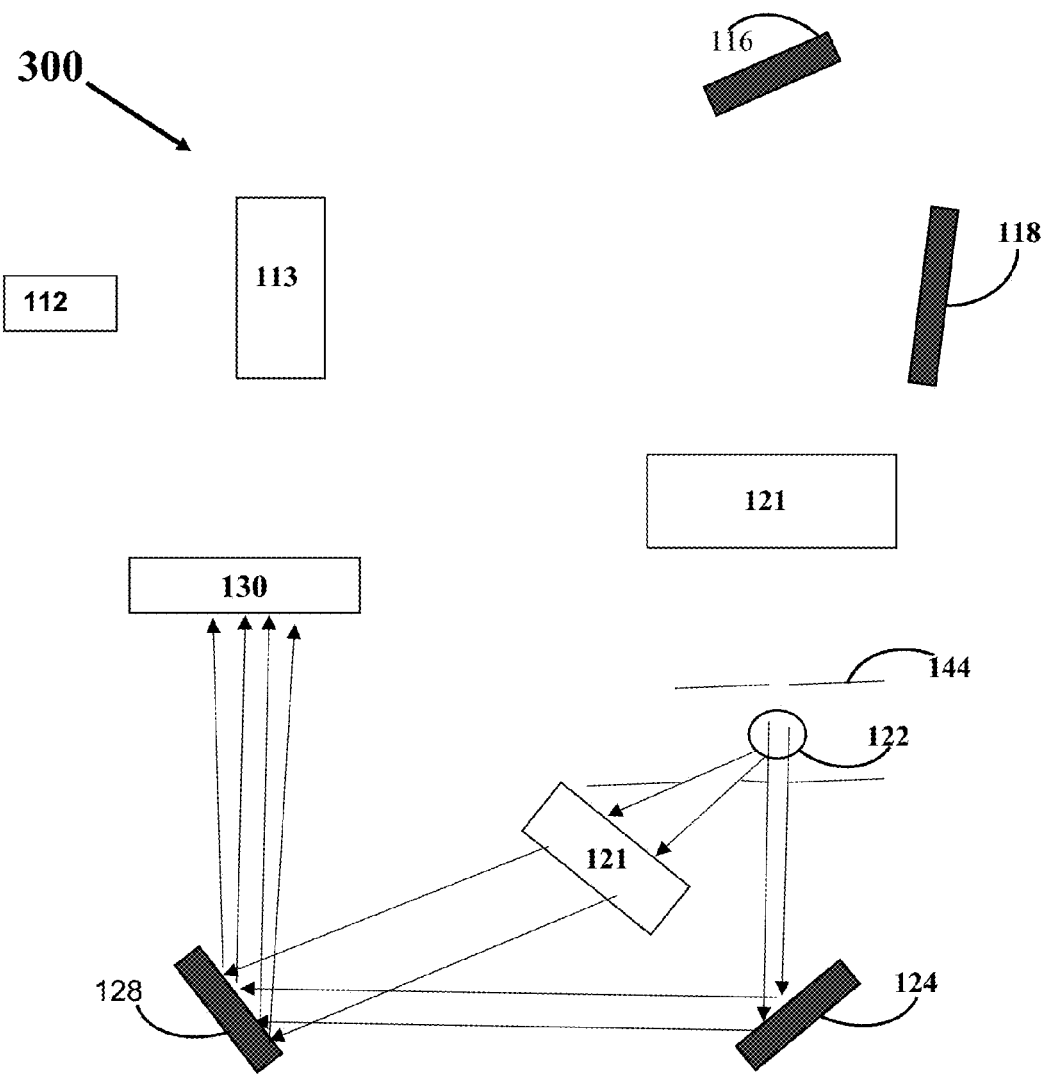
FIG. 3A illustrates elements of a device in a configuration for use in luminescence mode.
Figure 3B:
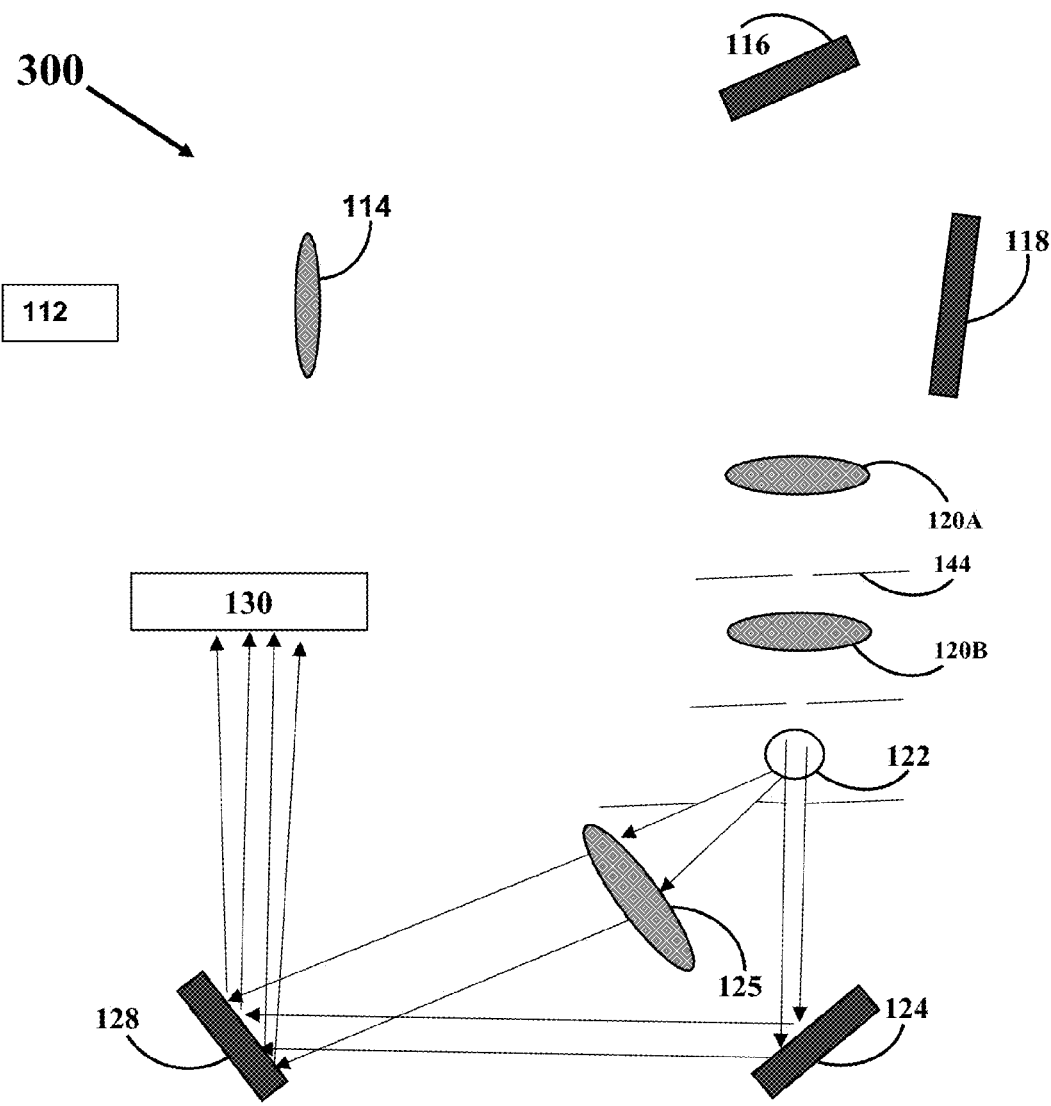
FIG. 3B illustrates elements of a device in a configuration for use in luminescence mode.

FIGS. 3A and 3B provide an illustration of embodiments of a device configuration (of a unified detection device capable of performing fluorometry, luminometry, and spectrometry as disclosed herein) for use in luminescence mode. In luminescence mode 300 as illustrated in FIGS. 3A and 3B:

A) Collection optics 125 (FIG. 3A) such as an off-axis collection lens 126 (FIG. 3B) collects light emitted (the emitted light being due to, e.g., bio-luminescence or chemi-luminescence) by the sample 122, and directs it to the second optical element 128 (configured to present a reflective face of second optical element 128, with the diffractive face (e.g., an emission path grating) oriented away from the light path). Light emitted (e.g., due to bio-luminescence or chemi-luminescence) by the sample 122 may also be directed to collection mirror 124, and directed by collection mirror 124 to the second optical element 128. Such a second optical element 128 may have an emission path grating or other dispersion element on one face and having a mirror surface on another face; in luminescence mode as shown in FIGS. 3A and 3B, the mirror surface of a second optical element 128 may be used to maximize the collection of luminescent light from the sample, and to direct that light to photodetector 130. The paths of the bio-luminescent or chemi-luminescent light emitted by the sample 122 are shown by the arrows directed towards collection mirror 124 and towards collection lens 126.

B) The collection mirror 124 and secondary mirror 128 direct the emitted light to the photodetector 130. The paths of the bio-luminescent or chemi-luminescent light following redirection by collection mirror 124 and collection lens 126 are shown by the single lines of arrows oriented towards second optical element 128. The paths of the bio-luminescent or chemi-luminescent light emitted by the sample 122 after its direction by second optical element 128 are shown by the single lines of arrows oriented towards photodetector 130.

Figure 4:
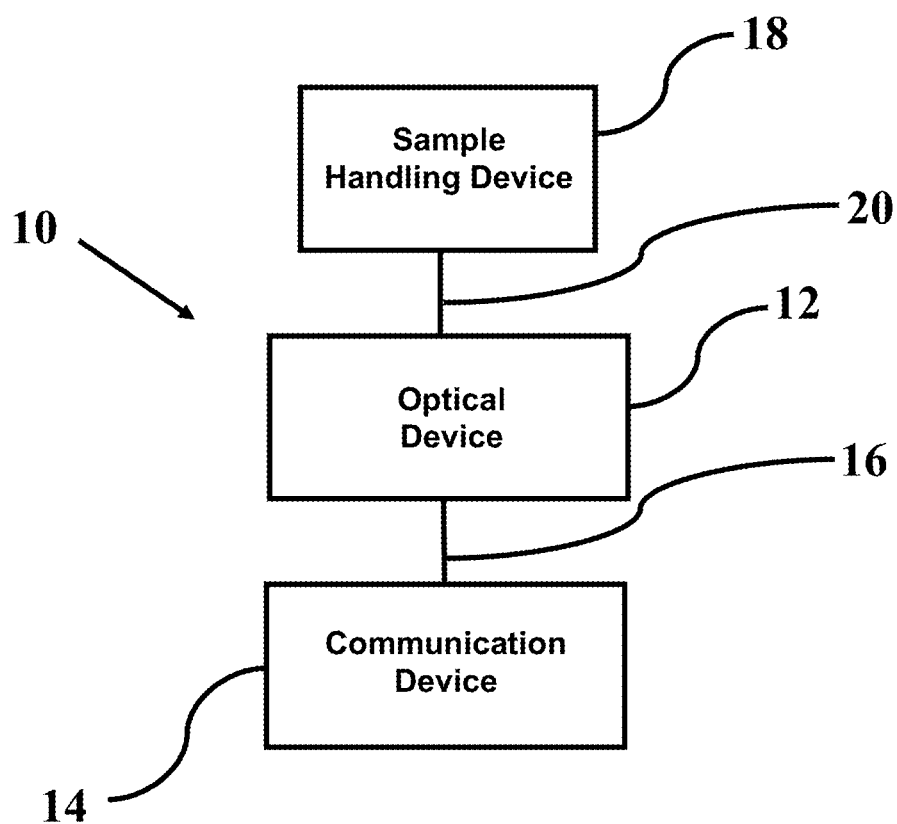
FIG. 4 illustrates elements of a system including a device as disclosed herein.

FIG. 4 illustrates an exemplary system which includes a unified detection device capable of performing fluorometry, luminometry, and spectrometry as disclosed herein. As illustrated in FIG. 4, a system 10 includes a unified detection device 12 as disclosed herein (labeled an "optical device" since unified detection devices as disclosed herein utilize optical techniques for observation, measurement or analysis of samples). It will be understood that a system 10 may include more than one unified detection device 12. It will be further understood that a system 10 (which includes a unified detection device 12) may include one or more further components, devices, or systems for use with a unified detection device 12, and that the further components, devices, and systems shown in FIG. 4 serve as illustrations of one of many suitable configurations and combinations of such further components, devices, or systems with a unified detection device 12.

A system 10 may include a communication device 14, which is operably connected to and in communication with the unified detection device 12 via communication channel 16, effective that information obtained by the unified detection device pursuant to its observation, measurement or analysis of samples may be communicated to a user, an external device, a database, a network, or other device or system. A user, external device, network, or other device or system may monitor, or may provide oversight of, a unified detection device 12 or its operation via a communication device 14 and a communication channel 16. A communication device 14, and a communication channel 16, may be effective to provide instructions to, or to otherwise control the operation of a unified detection device 12. A communication device 14 or a communication channel 16 may be present, and may be used, in addition to, or in place of, a communication component or a communication channel which may be included in a unified detection device 12 as disclosed herein.

A system 10 may include a sample handling device 18, which is operably connected to a unified detection device 12 by a linkage 20 effective that a sample (which may be a solid, fluid, gas, or other sample) is provided to the unified detection device 12 in a form and configuration suitable for observation, measurement, or analysis by the unified detection device 12. In embodiments, a sample handling device 18 may include a linkage with a unified detection device 12, so that a separate linkage 20 is not present, or is optional. A linkage of a sample handling device 18, or a linkage 20 may comprise, for example, a loading port or guide which aids in proper placement of a sample (or sample holder in which a sample may be retained or enclosed); or may comprise, for example, a mechanical system (e.g., a sample handling device) configured to transport a sample or sample holder from a first location to a second location, where the second location is a location within the unified detection device 12 suitable for observation, measurement, or analysis of the sample; or may otherwise enable positioning of a sample or sample holder in a unified detection device 12 for observation, measurement, or analysis.

In embodiments, a sample handling device 18 may include, or may be a part of, or may operate in conjunction with, a fluid handling device or a fluid handling system. For example, a fluid handling device or system may be configured to transfer a sample, a sample holder, a reagent vessel, or other object or container to or within a unified detection device. In embodiments, a fluid handling device or system may comprise a pipette configured to uptake, dispense, or transfer a biological sample. A fluid handling device or system may include, or may be linked to, other components, devices, or systems. A fluid handling device or system may include a plurality of pipette heads (where an individual pipette head includes a pipette nozzle configured to connect with a pipette tip that is removable from the pipette nozzle); one or more plungers that are individually movable, wherein at least one plunger is within a pipette head and is movable within the pipette head; and a motor configured to effect independent movement of individual plungers of the plurality. In embodiments, a pipette nozzle may be configured to connect with, or may include, an actuator configured to effect independent movement of one or more individual plungers. In embodiments, a fluid handling device or system may be configured to engage, or may include, a sample holder; and at least one pipette head, wherein an individual pipette head comprises a pipette nozzle configured to connect with the sample holder that is removable from said pipette nozzle, wherein the apparatus is operably connected to an image capture device that is configured to capture an image within or through the sample holder.

Mirror dispersion elements, as, e.g., illustrated by elements 128 shown in FIGS. 1A, 1B, 2A, 2B, 3A, and 3B, and as discussed above, have at least two faces, and include an optical dispersion element on one face and a reflective element on another face. A dispersion element of such mirror dispersion elements may be, e.g., a diffraction grating, or a prism (including a complex prism comprising two or more prism elements), or other optical dispersion element. A reflective element of such mirror dispersion elements may be a mirror, such as, e.g., a front surface mirror, or a back surface mirror, and may include both a front surface mirror and a back surface mirror.

Embodiments of mirror dispersion elements as disclosed herein are illustrated in FIGS. 5A and 5B. The mirror dispersion elements illustrated in FIG. 5A have reflective elements on one face and optically dispersive elements on another face. Such mirror dispersion elements may be rotated around an axis or otherwise moved effective to present either a reflective surface, or an optically dispersive surface, to light directed at the mirror dispersion element. In embodiments, a mirror dispersion element may be mounted on a movable mount in order that the mirror dispersion element may be rotated around an axis (e.g., an axis of a rotatable mount) or translated (e.g., moved in lateral, longitudinal, or a combination of lateral and longitudinal directions) effective to position a desired surface of the mirror dispersion elements in a proper position and orientation. The mirror dispersion elements illustrated in FIG. 5B have reflective elements and optically dispersive elements on the same face. Such mirror dispersion elements may be moved laterally or longitudinally, e.g., translated in at least one linear direction, effective to present either a reflective surface, or an optically dispersive surface, to light directed at the mirror dispersion element. In embodiments, a mirror dispersion element may be mounted on a translatable mount in order that the mirror dispersion element may be moved effective to position a desired surface of the mirror dispersion elements in a proper position and orientation. In embodiments, a mirror dispersion element may be mounted on a rotatable mount, on a translatable mount, or on a rotatable and translatable mount (i.e., a mount able to rotate around an axis and to translate in at least one linear direction). Any mirror dispersion element as disclosed herein may be mounted on a rotatable mount, on a translatable mount, or on a rotatable and translatable mount, regardless of whether the reflective surface and the optically dispersive surfaces are on different (e.g., opposite) sides of the mirror dispersion element, or are on the same side of the mirror dispersion element, or whether or not the mirror dispersion element may have multiple reflective surfaces, or multiple optically dispersive surfaces, or multiple reflective surfaces and multiple optically dispersive surfaces.

FIG. 5A illustrates exemplary embodiments of mirror dispersion elements as disclosed herein, showing different methods and configurations by which the combined mirror-dispersion element may be implemented. The embodiments illustrated in FIG. 5A have at least one reflective surface and one optically dispersive surface on opposite faces (opposite sides) of the mirror dispersion element. For example, in FIG. 5A, the embodiment labeled (i) illustrates a mirror dispersion element 51 having a reflective diffraction grating 511 held by adhesive layer 513 to mirror 515; in this embodiment, mirror 515 is a front surface mirror having a reflective surface 517. The embodiment labeled (ii) illustrates a mirror dispersion element 53 having a reflective diffraction grating 531 that is fabricated directly on mirror substrate 533 of mirror 535. In this embodiment, mirror 535 is a front surface mirror having a reflective surface 537. The embodiment labeled (iii) illustrates a mirror dispersion element 55 having a prism dispersion element 551 held by adhesive 553 to a mirror 555. In this embodiment, mirror 555 is a front surface mirror having a front reflective surface 557; in embodiments, mirror 555 may also have a further back reflective surface 559 (providing, in such embodiments, mirror 555 with a front reflective surface 557 as well as a back reflective surface 559). In alternative embodiments, a mirror dispersion element 55 may be a prism 551 alone, lacking a mirror 555. Including a mirror 555 along with a prism 551 increases optical dispersion by providing a longer optical path length than is provided by a prism 551 alone. The embodiment labeled (iv) illustrates a mirror dispersion element 57 having a compound prism dispersion element 571 held by adhesive 573 to a mirror 575 having a front reflective surface 577; in embodiments, a mirror 575 may have an optional back reflective surface 579. In alternative embodiments, a mirror dispersion element 57 may be a compound prism 571 alone, lacking a mirror 575. Including a mirror 575 along with a compound prism 571 increases optical dispersion by providing a longer optical path length than is provided by a compound prism 571 alone.

FIG. 5B illustrates exemplary embodiments of mirror dispersion elements as disclosed herein, showing different methods and configurations by which the combined mirror-dispersion element may be implemented. The embodiments illustrated in FIG. 5B have at least one reflective surface and one optically dispersive surface on the same face (same side)

of the mirror dispersion element. For example, in FIG. 5B, the embodiment labeled (a) illustrates a mirror dispersion element 52 having a reflective diffraction grating 521 held by adhesive layer 523 to mirror 525; in this embodiment, mirror 525 is a front surface mirror having a reflective surface 527. The embodiment labeled (b) illustrates a mirror dispersion element 54 having a reflective diffraction grating 541 that is fabricated directly on mirror substrate 543 of mirror 545. In this embodiment, mirror 545 is a front surface mirror having a reflective surface 547. The embodiment labeled (c) illustrates a mirror dispersion element 56 having a prism dispersion element 561 held by adhesive 563 to a mirror 565. In this embodiment, mirror 565 is a front surface mirror having a front reflective surface 567; in embodiments, mirror 565 may also have a further back reflective surface 569 (providing, in such embodiments, mirror 565 with a front reflective surface 567 as well as a back reflective surface 569). In alternative embodiments, a mirror dispersion element 56 may be a prism 561 alone, lacking a mirror 565. Including a mirror 565 along with a prism 561 increases optical dispersion by providing a longer optical path length than is provided by a prism 561 alone. The embodiment labeled (d) illustrates a mirror dispersion element 58 having a compound prism dispersion element 581 held by adhesive 583 to a mirror 585 having a front reflective surface 587; in embodiments, a mirror 585 may have an optional back reflective surface 589. In alternative embodiments, a mirror dispersion element 58 may be a compound prism 581 alone, lacking a mirror 585. Including a mirror 585 along with a compound prism 581 increases optical dispersion by providing a longer optical path length than is provided by a compound prism 581 alone.

Applicants disclose mirror dispersion elements, which are optical elements having a reflective surface (e.g., a mirror) and an optically dispersive surface (e.g., a prism or a diffraction grating). In embodiments, a prism may be a compound prism. Thus, mirror dispersion elements disclosed herein may have a plurality of surfaces, including at least two surfaces, including at least one surface that reflects light, and at least one surface that disperses (e.g., diffracts) light. It will be understood that the term light includes infrared, ultraviolet, and other wavelengths not visible to the normal human eye, in addition to visible wavelengths of light. In embodiments, a mirror dispersion element has an optically dispersive surface comprising a diffraction grating. In embodiments, a diffraction grating may be a reflective diffraction grating. In embodiments, a diffraction grating may be etched on a surface, or may be engraved on a surface, or may be provided on a surface by other means. In embodiments, a mirror dispersion element has an optically dispersive surface comprising a prism, which, in embodiments, may be a compound prism. In embodiments, a mirror dispersion element has a reflective surface, which may comprise a front surface mirror, a back surface mirror, or a reflective surface comprising both a front surface mirror and a back surface mirror.

In embodiments, Applicants disclose devices comprising a mirror dispersion element, or multiple mirror dispersion elements. Thus, Applicants disclose devices comprising at least one mirror dispersion element, wherein the mirror dispersion element has a plurality of faces, comprising a first face having a reflective surface, and a second face comprising an optically dispersive surface (e.g., a surface comprising an optical dispersion element). In embodiments of such devices, the mirror dispersion element is mounted on a movable mount (which may be, e.g., a rotatable mount, a translatable mount, or other movable mount).

In embodiments, a device comprising at least one mirror dispersion element includes an optical path, and at least one mirror dispersion element is disposed so that the optical path impinges on the mirror dispersion element. The mirror dispersion element may present a reflective surface to the optical path, reflecting light in a desired direction when light traveling along the light path contacts the reflective surface. Rotation of the mirror dispersion element on a rotatable mount is effective to present an optically dispersive surface to the optical path, diffracting light in a desired direction when light traveling along the light path contacts the optically dispersive surface. Further rotation of the mirror dispersion element may bring the previously used reflective surface back into the optical path, or may bring a further surface, which may be a reflective surface, a diffractive (or other optically dispersive) surface, or which may have other optical properties.

In embodiments of such devices, the mirror dispersion element is mounted on a translatable mount, configured for linear translation in one, or two, or more directions. In embodiments, a device comprising at least one mirror dispersion element includes an optical path, and at least one mirror dispersion element is disposed so that the optical path impinges on the mirror dispersion element. The mirror dispersion element may present a reflective surface to the optical path, reflecting light in a desired direction when light traveling along the light path contacts the reflective surface. Translation of the mirror dispersion element on a translatable mount is effective to present an optically dispersive surface to the optical path, diffracting light in a desired direction when light traveling along the light path contacts the optically dispersive surface. Further translation of the mirror dispersion element may bring the previously used reflective surface back into the optical path, or may bring a further surface, which may be a reflective surface, a diffractive (or other optically dispersive) surface, or which may have other optical properties.

A mirror dispersion element may be mounted on any movable mount, such as, e.g., a rotatable, translatable, or other movable mount. A rotatable, translatable, or other movable mount may be moved by any suitable means. In embodiments, a mirror dispersion element may be mounted on a piezoelectric mount, which mirror dispersion element may be moved upon activation of a piezoelectric element of such a mount. In embodiments, a mirror dispersion element may be mounted on a mount that is operably connected to, or part of, a stepping motor, which mirror dispersion element may be moved upon activation of the motor element of such a mount. In embodiments, a mirror dispersion element may be mounted on an electromagnetic, pneumatic or hydraulic mount, or connected to an electromagnetic, pneumatic or hydraulic element, which mirror dispersion element may be moved upon activation of the electromagnetic, pneumatic, or hydraulic elements of such a mount.

In embodiments of devices comprising a mirror dispersion element as disclosed herein, the mirror dispersion element may have an optical dispersion element comprising a grating, or comprising a prism. In embodiments, such a prism may be a compound prism. In embodiments, a grating may be etched on a surface to provide a diffractive surface, or may be engraved on a surface to provide a diffractive surface, or may include portions of etched and of engraved gratings. In embodiments, a grating may be dyed on a surface to provide a diffractive surface. In embodiments, a grating may be lithographed on a surface to provide a diffractive surface. In embodiments of devices comprising a mirror dispersion element as disclosed herein, the mirror dispersion element may comprise a mirror; in embodiments, such a mirror may be a back surface mirror, may be a front surface mirror, and may include both a back surface mirror and a front surface mirror.

In embodiments, mirror dispersion elements may be of any suitable size; for example, the size of mirror dispersion elements and the component parts (e.g., mirrors, prisms, and gratings) used for the devices and systems disclosed herein, and the size of other components (including, e.g., lenses and other elements) can be anywhere from micron scale (fabricated and operated by micro-electro-mechanical systems (MEMS) processes for example), up to benchtop level components (several millimeters to centimeters). In embodiments, prisms may be fabricated from glass (e.g. a borosilicate glass such as BK7 glass, an aluminosilicate glass, a soda glass, Fused Silica, a flint glass such as SF11, and other glasses), or plastic such as a polymer (such as, e.g., poly(methyl methacrylate) (PMMA), polycarbonate, polystyrene, cyclo-olefin polymers (COP), cyclo-olefin co-polymers (COC), and other polymers). The choice of whether to use a glass or a polymer for a prism or other diffractive element may be determined by consideration of such factors as the optical dispersion of the material, the optical transmission of the material, optical losses due to the material, the weight of the material, the desired size of the mirror dispersion element, the cost of the material, the strength of the material, and other characteristics and requirements. Mirrors may be fabricated on glass or plastic (including such polymers as are listed above regarding prisms) substrates, or may be fabricated on metal substrates (such as aluminum, steel, gold, silver, copper, or other metal substrate). The surfaces of a mirror substrate must be ground or polished or both to the required surface smoothness level, which smoothness level is determined by the reflectivity requirements.

Mirrors made from metallic substrates typically do not need to be coated, where such substrates have been polished to the desired reflection characteristics. In embodiments, a metal mirror substrate may be coated with a thin film of aluminum, enhanced aluminum, gold, silver, dielectric material, or other reflective coating for improved reflection characteristics (i.e., in a manner similar to the coatings that may be applied to glass or polymer substrates). Such coatings may be applied to the reflective surfaces of gratings and prisms as well. In embodiments, dielectric thin film coatings may be used to improve the reflection or to improve the transmission characteristics of an optical element or portion thereof.

Mirror dispersion elements may be prepared by combining a mirror with a prism or diffraction element, and may be prepared by treating different surfaces of a mirror dispersion element to provide suitable reflective properties at one surface and suitable diffractive, refractive, or otherwise dispersive properties at another surface. Reflective surfaces may be prepared by any suitable means, including, for example, polishing or smoothing the surface by other means. In embodiments, a reflective surface may include a reflective coating; a reflective coating may include a coating of gold, or silver, or aluminum, or copper, or a dielectric material, or silicon dioxide, or a metal oxide, or combinations thereof, or other materials or combination of materials providing a reflective surface. Prisms, including compound prisms, and diffraction gratings may be uncoated, or may include such coatings, or other coatings providing or enhancing diffraction or refraction of light. Diffraction gratings may include surface etchings, surface engravings, or other surface features and treatments which provide or enhance diffraction of light.

In embodiments, diffraction gratings may include dyed, lithographed, etched or ground lines or grooves. The spacing between these lines or grooves may be determined by the dispersion requirements of the design. For example, for a relatively large 100 millimeter (mm) path-length, there may be between about 200 lines to about 1000 lines per mm, or may be between about 400 lines to about 800 lines per mm, and in embodiments may be about 600 lines per mm.

In embodiments, optically transmissive elements (including lenses, prisms, filters, and other optical elements configured to allow light to pass through the element) may be fabricated from glass (e.g. a borosilicate glass such as BK7 glass, an aluminosilicate glass, a soda glass, Fused Silica, a flint glass such as SF11, and other glasses), or plastic such as a polymer (such as, e.g., poly(methyl methacrylate) (PMMA), polycarbonate, polystyrene, cyclo-olefin polymers (COP), cyclo-olefin co-polymers (COC), and other polymers), or other optically transmissive material. The choice of whether to use a glass or a polymer or other material may be determined by consideration of the relevant optical characteristics of the material, including the optical transmission of the material, the losses incurred by transmission of light through the material, the weight, cost, and strength of the material, the desired size of the optical element, and other characteristics and requirements.

Any suitable wavelength of light, or any suitable wavelength range may be used. In embodiments, the light used (e.g., provided by a light source, emitted by a luminescent source, or detected by an optical detector) in and by a unified detection system as disclosed herein, and by component elements thereof, may be light having wavelengths of between about 100 nanometer (nm) to about 1500 nm, or between about 200 nm to about 1000 nm (i.e., a range including ultraviolet, visible, and infrared wavelengths).

In embodiments, for example, where mirror dispersion elements are prepared by combining a mirror with a prism or diffraction element, a mirror and a prism, or a mirror or other diffraction element may be fixed to each other with an adhesive. Such an adhesive may be, for example, a cyanoacrylate adhesive, an epoxy adhesive, a silicone adhesive, a urethane adhesive, an adhesive cured using ultraviolet light, an adhesive tape, or other adhesive.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not.

The appended claims are not to be interpreted as including means-plus-function limitations, unless such a limitation is explicitly recited in a given claim using the phrase "means for."

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2014-2015 Theranos, Inc.

The invention claimed is:

1. A unified detection device for fluorometry, luminometry, and spectrometry, comprising:
   a first optical element comprising a diffractive surface movably mounted on a first movable mount;
   a first mirror configured for reflecting light after contact of said light with said diffractive surface;
   a first lens configured for focusing or for collimating light reflected from said first mirror;
   a second mirror movably mounted on a second movable mount;
   a second optical element movably mounted on a third movable mount, said second optical element having a first face and a second face, said first face having a reflective surface configurable to reflect light from said second mirror, and said second face having a diffractive surface configurable to diffract light from said second mirror;
   a second lens configured for directing light to or onto said second optical element, wherein the second lens is positioned to collect light off-axis relative to a direct light path from the first lens to the second mirror; and
   a photodetector receiving light from the second optical element;
   wherein the second mirror has a first configuration to reflect light from the first lens to the second optical element and a second configuration to reflect light from the first lens in a direction away from the second optical element.

2. The unified detection device of claim 1, further comprising a sample holder configured to hold a sample for optical observation, measurement, or analysis.

3. The unified detection device of claim 1, further comprising a sample handling device configured to transport a sample or a sample holder to a location suitable for optical observation, measurement, or analysis.

4. The unified detection device of claim 3, wherein i) said sample handling device comprises a fluid handling device or system configured to transport a sample or a sample holder, or ii) said sample handling device is configured to operate with a fluid handling device or system configured to transport a sample or a sample holder.

5. The unified detection device of claim 1, wherein said diffractive surface comprises a grating or a prism.

6. A system for fluorometry, luminometry, and spectrometry comprising a unified detection device of claim 1, a communication device, and a communication channel operably connecting said device with said communication device.

7. The system for fluorometry, luminometry, and spectrometry of claim 6, further comprising a sample handling device configured to transport a sample or a sample holder to a location suitable for optical observation, measurement, or analysis.

8. The system for fluorometry, luminometry, and spectrometry of claim 7, wherein said sample handling device is configured to operate with a fluid handling device or system configured to transport a sample.

* * * * *